(12) United States Patent
Munneke et al.

(10) Patent No.: US 6,719,689 B2
(45) Date of Patent: Apr. 13, 2004

(54) METHOD AND SYSTEM FOR COMPRESSING AND STORING DATA IN A MEDICAL DEVICE HAVING LIMITED STORAGE

(75) Inventors: Dave Munneke, Brooklyn Park, MN (US); Harry B. A. Kerver, Duiven (NL)

(73) Assignee: Medtronic, Inc., Minneapolis, MN (US)

( * ) Notice: Subject to any disclaimer, the term of this patent is extended or adjusted under 35 U.S.C. 154(b) by 364 days.

(21) Appl. No.: 09/847,049

(22) Filed: Apr. 30, 2001

(65) Prior Publication Data

US 2002/0193668 A1 Dec. 19, 2002

(51) Int. Cl.⁷ ................................................ A61B 5/04
(52) U.S. Cl. .......................... 600/300; 607/4; 600/509
(58) Field of Search ................... 600/300, 301, 600/509, 523, 524, 902, 521, 522; 607/4, 5, 9

(56) References Cited

U.S. PATENT DOCUMENTS

| 4,716,903 A | * | 1/1988 | Hansen et al. |
| 4,920,489 A | * | 4/1990 | Hubelbank et al. |
| 5,215,098 A | * | 6/1993 | Steinhaus et al. |
| 5,217,021 A | * | 6/1993 | Steinhaus et al. |
| 5,263,486 A | * | 11/1993 | Jeffreys |
| 5,312,446 A | * | 5/1994 | Holschbach et al. |
| 5,603,331 A | * | 2/1997 | Heemels et al. |
| 5,623,935 A | * | 4/1997 | Faisandier |
| 5,694,356 A | * | 12/1997 | Wong et al. |
| 5,709,216 A | * | 1/1998 | Woodson, III |
| 5,735,285 A | * | 4/1998 | Albert et al. |
| 5,819,740 A | * | 10/1998 | Muhlenberg |
| 5,836,889 A | * | 11/1998 | Wyborney et al. |
| 5,836,982 A | * | 11/1998 | Muhlenberg et al. |

* cited by examiner

*Primary Examiner*—Jeffrey R. Jastrzab
(74) *Attorney, Agent, or Firm*—Girma Wolde-Michael

(57) ABSTRACT

A method for compressing data in an implantable device is provided. A current data sample is received. A difference value is determined between the current data sample and a previous data sample. The current data sample is compressed to at least one output symbol based on the difference value between the current sample and the previous data sample. Systems and programs of using the method are also provided.

64 Claims, 11 Drawing Sheets

METHOD AND SYSTEM FOR COMPRESSING AND STORING DATA IN A MEDICAL DEVICE HAVING LIMITED STORAGE

FIELD OF THE INVENTION

The present invention relates to the field of medical devices with limited data storage capacity. More particularly, the present invention relates to implantable devices, such as cardiac pacing systems, that are capable of compressing and storing data, especially cardiac signal data such as episodes of intracardiac electro cardiogram (IEGM).

BACKGROUND OF THE INVENTION

Medical devices with limited data storage capacity are well known in the art. Two common examples are hearing aids and pacemakers. In the latter case, some pacemakers, or other such implantable pulse generators (IPGs) include means for storing data related to cardiac events. These cardiac events may include, for example, episodes of spontaneous heart rate that are higher or lower than an acceptable or previously established rate. Stored data related to one or more cardiac events are useful in assessing the functioning of the IPG and in monitoring the progress of the patient.

Digital signal processing (DSP) has proved to be a useful tool in the environment of medical devices such as implantable pulse generators. Using DSP technology, an incoming sensed heart signal may be converted to a digital signal, e.g., an 8-bit signal. This conversion may occur at a predetermined sample rate. For example, episodes of IEGM may be processed using DSP. The IEGM is one type of signal in which heart contractions may be identified.

Typically an input signal from an IPG is amplified. The signal may then be converted to a digital signal (using, for example, analog to digital (A/D) converters). Then the signal may be digitally processed, generally by filtering the resulting digital data streams. The result from this process is generally a number of digital data streams. Each data stream is more or less a digitally processed representation of an IPG input signal. Based upon the information in these streams, DSP technology may be used to determine heart contractions. As stated above, a physician may use information about these contractions to assess and monitor the efficacy of IPG therapy.

Typically, data is collected continuously while the patient is using the IPG. However, a physician is only able to view the data when the patient and the IPG are available for evaluation, e.g. when the patient is in the physician's office. Usually, the IPG is linked to an interrogation device with a display, which shows the data being collected at the time the patient is being examined.

However, the most interesting episodes of IEGM generally occur when the patient is proceeding about his normal business, away from the physician's office. Thus, current IPGs (and other implantable therapeutic devices) have the capability to store data, such as an IEGM, for later viewing by the physician. At the time of viewing, the IPG may be linked to an interrogation device with a display that communicates the stored data. Because implantable devices are, of necessity, small enough for implantation in a human body, their available storage space is limited. Thus, the signal, such as a digital IEGM, needs to be compressed as much as possible without losing the sense of the original signal. Moreover, the type of information stored is also important in analysis of the efficacy of IPG therapy. For example, storage of an episode may begin when a preset condition, or "trigger", has been met, e.g. the IPG senses a particular heart rate indicative of a cardiac event such as an atrial fibrillation. Although data representing the cardiac event, or trigger, itself may be of interest to the physician, analysis of the data representing cardiac conditions prior to the event may be more useful in assessing the device's performance and the disease's progress. Thus, the ability to store data prior to the "trigger" event is also desirable. The longer the stored episode, particularly prior to the "trigger", the more useful the data is to the physician. Again, efficient compression would allow longer episodes to be stored.

Thus, a need exists in the medical arts for compressing and storing data in an implantable medical device.

Several methods have been proposed in the prior art for improving compression and storage in an implantable medical device.

For example, U.S. Pat. No. 5,603,331 to Heemels et al., entitled "Data Logging System For Implantable Cardiac Device" discloses the compression of heart rate variability data via logarithmic data compression and the storing of the results as time-related histograms with a standard deviation.

U.S. Pat. No. 5,819,740 to Muhlenberg entitled "System and Method for Compressing Digitalized Signals in Implantable and Battery-Powered Devices" discloses the compression of data using non-linear sampling. A time varying threshold is used and the signal of interest is compared to the threshold.

U.S. Pat. No. 5,836,982 to Muhlenberg et al., entitled "System and Method of Data Compression and Non-Linear Sampling from Implantable and Battery-Powered Devices" discloses compressing a data block by storing the change, or delta, from one sample to another sample.

U.S. Pat. No. 5,312,446 to Holschbach et al., entitled "Compressed Storage of Data in Cardiac Peacemakers" discloses compression of data using an analog implementation of a turning point algorithm.

U.S. Pat. No. 5,623,935 to Faisandier entitled "Data Compression Methods and Apparatus for Use with Physiological Data" discloses compression of data by generating the first and second derivatives of an analog signal. The first and second derivatives of an analog signal are generated and one of three modes of encoding is selected. Either one of the derivative values is then encoded using one of the three modes based upon maximum compression.

U.S. Pat. No. 5,709,216 to Woodson entitled "Data Reduction of Sensed Values in an Implantable Medical Device Through the Use of a Variable Resolution Technique" discloses compression of data using variable resolution. The variable resolution is based upon pre-selected sub-ranges, i.e., smaller values or intervals have finer resolutions.

U.S. Pat. No. 5,215,098 to Steinhause et al., entitled "Data Compression of Cardiac Electrical Signals Using Scanning Correlation and Temporal Data Compression" discloses data compression by storing pre-recorded (i.e. learned) signal templates.

U.S. Pat. No. 5,217,021 to Steinhause et al., entitled "Detection of Cardiac Arrhythmias Using Correlation of a Cardiac Electrical Signal and Temporal Data Compression" also discloses data compression using stored pre-recorded signal templates.

U.S. Pat. No. 5,836,889 to Wyborny et al., entitled "Method and Apparatus for Storing Signals in an Implantable Medical Device" discloses compression of data for storing a straight-line connection between the last stored value and new data. Data is stored when the first derivative exceeds a threshold.

U.S. Pat. No. 4,716,903 to Hanson et al., entitled "Storage in a Pacemaker Memory" discloses data compression by storing the time to the next sample. The time is stored when the samples are near the baseline. An additional flag is added for turning points.

U.S. Pat. No. 5,263,486 to Jeffreys entitled "Apparatus and Method for Electrocardiogram Data Compression" discloses data compression by varying the sampling period dynamically. The variation is based upon signal rate of change value.

U.S. Pat. No. 4,920,489 to Hubelbank et al., entitled "Apparatus and Method for Solid State Storage of Episodic Signals" discloses compression of data by storing the derivative value, which is defined as data differing from the last stored value. The resolution is also changed based upon the magnitude of rate change.

U.S. Pat. No. 5,735,285 to Albert et al., entitled "Method and Hand-Held Apparatus for Demodulating and Viewing Frequency Modulated Biomedical Signals" discloses transmission of data using A-Law encoding and decoding.

U.S. Pat. No. 5,694,356 to Wong et al., entitled "High Resolution Analog Storage EPROM and Flash EPROM" discloses compression of a signal using A-Law or U-Law log arrhythmic relationships.

As discussed above, the most pertinent prior art patents are shown in the following table:

TABLE 1

| Prior Art Patents. | | |
|---|---|---|
| U.S. Pat. No. | Date | Inventor(s) |
| 5,836,982 | Nov. 17, 1998 | Muhlenberg et al. |
| 5,836,889 | Nov. 17, 1998 | Wyborney et al. |
| 5,819,740 | Oct. 13, 1998 | Muhlenberg |
| 5,735,285 | Apr. 7, 1998 | Albert et al. |
| 5,709,216 | Jan. 20, 1998 | Woodson, III |
| 5,694,356 | Dec. 2, 1997 | Wong et al. |
| 5,623,935 | Apr. 29, 1997 | Faisandier |
| 5,603,331 | Feb. 18, 1997 | Heemels et al. |
| 5,312,446 | May 17, 1994 | Holschbach et al. |
| 5,263,486 | Nov. 23, 1993 | Jeffreys |
| 5,217,021 | Jun. 8, 1993 | Steinhaus et al. |
| 5,215,098 | Jun. 1, 1993 | Steinhaus et al. |
| 4,920,489 | Apr. 24, 1990 | Hubelbank et al. |
| 4,716,903 | Jan. 5, 1988 | Hansen et al. |

All the patents listed in Table 1 are hereby incorporated by reference herein in their respective entireties. As those of ordinary skill in the art will appreciate readily upon reading the Summary of the Invention, the Detailed Description of the Preferred Embodiments and the claims set forth below, many of the devices and methods disclosed in the patents of Table 1 may be modified advantageously by using the teachings of the present invention.

SUMMARY OF THE INVENTION

The present invention is therefore directed to providing a method and system for compressing and storing data in an implantable medical device, such as a cardiac pacing device. The system of the present invention may overcome at least some of the problems, disadvantages and limitations of the prior art described above, and provides a more efficient and accurate means of compressing and storing data, such as heart signal data, in an implantable medical device.

The present invention has certain objects. That is, various embodiments of the present invention provide solutions to one or more problems existing in the prior art respecting the pacing of cardiac tissue. Those problems include, without limitation: (a) limited data storage capacity of an implantable device; (b) limited data compression capabilities of an implantable device; (c) difficulty in distinguishing data which may indicate or precede a trigger event; (d) difficulty in determining which direction to encode or decode the data stream (e) variability in data values being compressed or otherwise processed by an implantable medical device; and (f) difficulty in identifying start of storage location, end of storage location and/or significant event location in a particular data stream being compressed.

In comparison to known techniques for storing data in an implantable device, various embodiments of the present invention may provide one or more of the following advantages: (a) increased data storage capacity in an implantable device; (b) efficient and accurate processing of data streams in an implantable device; (c) ability to compress and store of data streams that include markedly differing values in an implantable device; (d) ability to indicate a value corresponding to a significant event, a start of storage and/or an end of storage; and (e) the ability to store efficiently data and identify data gathered before and/or including a significant event.

Some of the embodiments of the present invention include one or more of the following features: (a) an implantable device with increased data storage capacity; (b) an implantable device capable of efficient compression and storage of data streams that include markedly differing values; (c) an implantable device capable of indicating the location of a significant event value, a start of storage value and/or an end of storage value within a data stream; (d) methods for compressing data streams that include markedly differing values; (e) methods of compressing data streams in which the location of a significant event value, a start of storage value and/or an end of storage value are indicated within the compressed data stream; and (f) methods of identifying data gathered before and/or including a significant event.

At least some embodiments of the present invention involve receiving a current data sample. A difference value is determined between the current data sample and a previous data sample. The previous data sample may also be received. The current data sample is compressed to at least one output symbol based on the difference value between the current sample and the previous data sample. The series of output symbols may comprise more than one character. The amplitude resolution of the current data sample may be reduced. A sequence of similar output symbols may be converted to an escape output symbol. The series of output symbols may be converted to a variable bit length code. An absolute reference value may be inserted after the current sample.

BRIEF DESCRIPTION OF THE DRAWINGS

The above, and other objects, advantages and features of the present invention will be more readily understood from the following detailed description of the preferred embodiments thereof, when considered in conjunction with the drawings, in which like reference numerals indicate identical structures throughout the several views, and wherein.

DETAILED DESCRIPTION OF THE PRESENTLY PREFERRED EMBODIMENTS

It is to be understood that the terms "IPG" and "IMD", as employed in the specification and claims hereof, means an implantable medical device capable of delivering electrical stimuli to cardiac tissue, and includes within its scope pacemakers, PCDs, ICDs, etc.

Figure 1:
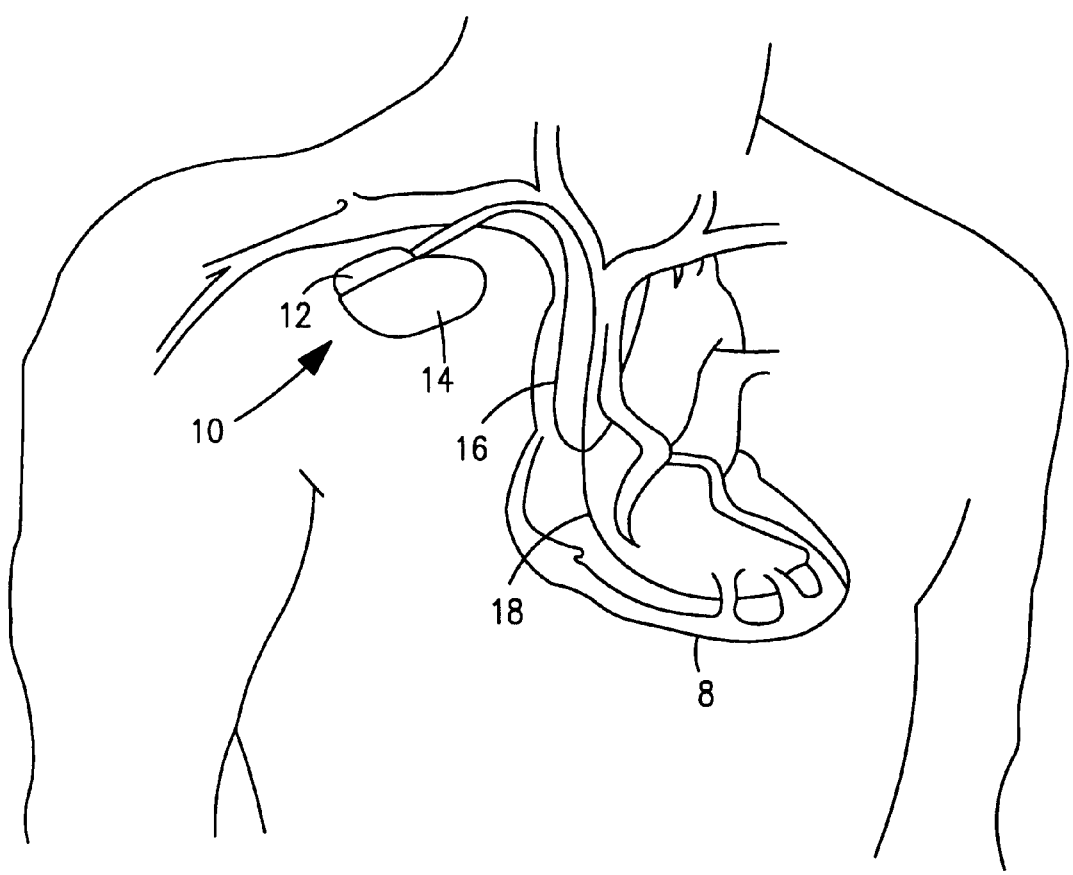
FIG. 1 is a schematic view of one embodiment of an implantable medical device in situ, made in accordance with the present invention.

FIG. 1 is a simplified schematic view of one embodiment of implantable medical device ("IMD") 10 of the present invention. The IMD 10 shown in FIG. 1 is a pacemaker comprising at least one of pacing and sensing leads 16 and 18. Leads 16, 18 may be attached to hermetically sealed enclosure 14 and may be implanted near heart 8. Pacing lead 16 and sensing lead 18 may sense electrical signals attendant to the depolarization and re-polarization of the heart 8, and further provide pacing pulses for causing depolarization of cardiac tissue in the vicinity of the distal ends thereof. Leads 16 and 18 may have unipolar or bipolar electrodes disposed thereon, as is well known in the art. Examples of IMD 10 include implantable cardiac pacemakers disclosed in U.S. Pat. No. 5,158,078 to Bennett et al., U.S. Pat. No. 5,312,453 to Shelton et al. or U.S. Pat. No. 5,144,949 to Olson, all of which are hereby incorporated by reference, each in their respective entireties.

Figure 2:
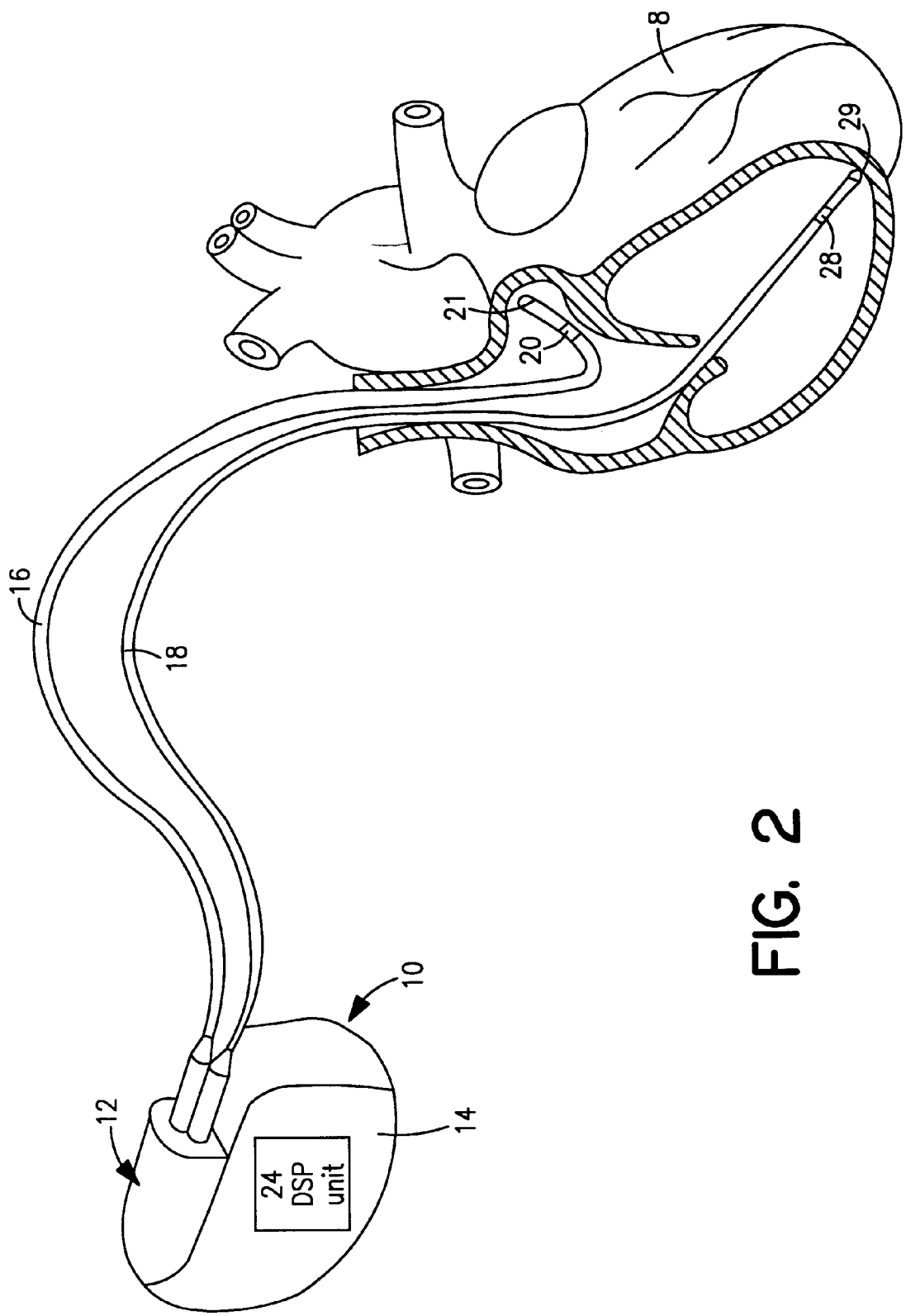
FIG. 2 is another schematic view of an embodiment of the implantable medical device of FIG. 1, made in accordance with the present invention.

FIG. 2 shows connector module 12 and hermetically sealed enclosure 14 of IMD 10 located in and near human or mammalian heart 8. Atrial and ventricular pacing leads 16 and 18 extend from connector header module 12 to the right atrium and ventricle, respectively, of heart 8. Atrial electrodes 20 and 21 disposed at the distal end of atrial pacing lead 16 are located in the right atrium. Ventricular electrodes 28 and 29 at the distal end of ventricular pacing lead 18 are located in the right ventricle. As seen in FIG. 2, IMD 10 may also include or be in communication with a digital signal processing (DSP) unit 24.

Figure 3:
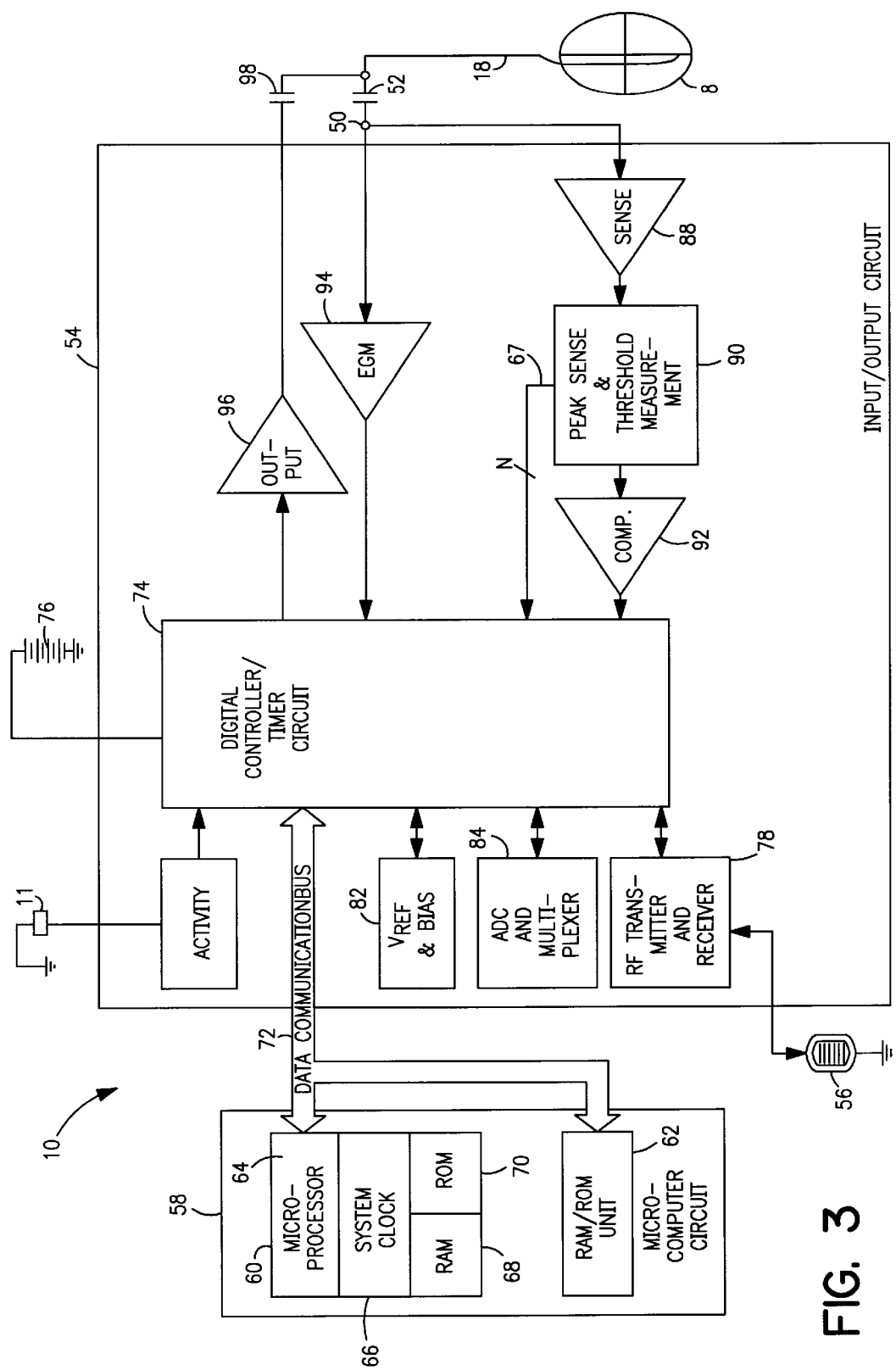
FIG. 3 is a block diagram illustrating components of an embodiment of the implantable medical device of FIG. 1, made in accordance with the present invention.

FIG. 3 shows a block diagram illustrating the constituent components of IMD 10 in accordance with one embodiment of the present invention, where IMD 10 is a pacemaker having a microprocessor-based architecture. IMD 10 is shown as including activity sensor 11. Activity sensor 11 may be, for example, an accelerometer based on silicon technology, a piezoceramic accelerometer or an accelerometer bonded to a hybrid circuit located inside enclosure 14. Activity sensor 11 typically (although not necessarily) provides a sensor output that varies as a function of a measured parameter relating to a patient's metabolic requirements. For the sake of convenience, IMD 10 in FIG. 3 is shown with lead 18 only connected thereto; similar circuitry and connections not explicitly shown in FIG. 3 apply to lead 16.

IMD 10 in FIG. 3 is most preferably programmable by means of an external programming unit (not shown in the Figures). One such programmer is the commercially available Medtronic Model 9790 programmer, which is microprocessor-based and provides a series of encoded signals to IMD 10, typically through a programming head which transmits or telemeters radio-frequency (RF) encoded signals to IMD 10. Such a telemetry system is described in U.S. Pat. No. 5,312,453 to Wyborny et al., hereby incorporated by reference in its entirety. The programming methodology disclosed in the '453 patent is identified herein for illustrative purposes only. Any of a number of suitable programming and telemetry methodologies known in the art may be employed so long as the desired information is transmitted to and from the pacemaker.

As shown in FIG. 3, lead 18 is coupled to node 50 in IMD 10 through input capacitor 52. Activity sensor or accelerometer 11 is most preferably attached to a hybrid circuit located inside hermetically sealed enclosure 14 of IMD 10. The output signal provided by activity sensor 11 is coupled to input/output circuit 54. Input/output circuit 54 contains analog circuits for interfacing to heart 8, activity sensor 11, antenna 56 and circuits for the application of stimulating pulses to heart 8. The rate of heart 8 may be controlled by software-implemented algorithms stored in microcomputer circuit 58.

Microcomputer circuit 58 preferably comprises on-board circuit 60 and off-board circuit 62. Circuit 58 may correspond to a microcomputer circuit disclosed in U.S. Pat. No. 5,312,453 to Shelton et al., hereby incorporated by reference in its entirety. On-board circuit 60 preferably includes microprocessor 64, system clock circuit 66 and on-board RAM 68 and ROM 70. Off-board circuit 62 preferably comprises a RAM/ROM unit. On-board circuit 60 and off-board circuit 62 are each coupled by data communication bus 72 to digital controller/timer circuit 74. Microcomputer circuit 58 may comprise a custom integrated circuit device augmented by standard RAM/ROM components.

Electrical components shown in FIG. 3 may be powered by an appropriate implantable battery power source 76 in accordance with common practice in the art. For the sake of clarity, the coupling of battery power to the various components of IMD 10 is not shown in the Figures. Antenna 56 is connected to input/output circuit 54 to permit uplink/downlink telemetry through RF transmitter and receiver telemetry unit 78. By way of example, telemetry unit 78 may correspond to that disclosed in U.S. Pat. No. 4,566,063, issued to Thompson et al. and hereby incorporated by reference in its entirety, or to that disclosed in the above-referenced '453 patent. In one embodiment of the invention, the particular programming and telemetry scheme selected permits the entry and storage of cardiac rate-response parameters. The specific embodiments of antenna 56, input/output circuit 54 and telemetry unit 78 presented herein are shown for illustrative purposes only, and are not intended to limit the scope of the present invention.

Continuing to refer to FIG. 3, $V_{REF}$ and bias circuit 82 most preferably generate stable voltage reference and bias currents for analog circuits included in input/output circuit 54. Analog-to-digital converter (ADC) and multiplexer unit 84 digitizes analog signals and voltages to provide "realtime" telemetry intracardiac signals and battery end-of-life (EOL) replacement functions. Once signals have been converted to multi-bit digital signals by A/D converter 57, they may be sent to storage in RAM (memory) 59 under control of direct memory access circuit 61. Microprocessor 51 may employ digital signal analysis techniques to characterize the digitized signals stored in RAM (memory) 59 to recognize and classify the patient's heart rhythm employing any of the numerous signal-processing methodologies known to the art.

Operating commands for controlling the timing of IMD 10 are coupled by data communication bus 72 to digital controller/timer circuit 74, where digital timers and counters establish the overall escape interval of the IMD 10 as well as various refractory, blanking and other timing windows for controlling the operation of peripheral components disposed within input/output circuit 54.

Digital controller/timer circuit 74 is preferably coupled to sensing circuitry, including sense amplifier 88, peak sense and threshold measurement unit 90 and comparator/threshold detector 92. Circuit 74 is further preferably coupled to electrogram (EGM) amplifier 94 for receiving amplified and processed signals sensed by lead 18. Sense amplifier 88 amplifies sensed electrical cardiac signals and provides an amplified signal to peak sense and threshold measurement circuitry 90, which in turn provides an indication of peak sensed voltages and measured sense amplifier threshold voltages on multiple conductor signal path 67 to digital controller/timer circuit 74. An amplified sense amplifier signal is then provided to comparator/threshold detector 92. By way of example, sense amplifier 88 may correspond to that disclosed in U.S. Pat. No. 4,379,459 to Stein, hereby incorporated by reference in its entirety.

The electrogram signal provided by EGM amplifier 94 is employed when IMD 10 is being interrogated by an external programmer to transmit a representation of a cardiac analog electrogram. See, for example, U.S. Pat. No. 4,556,063 to Thompson et al., hereby incorporated by reference herein in its entirety. Output pulse generator 96 provides pacing stimuli to patient's heart 8 through coupling capacitor 98 in response to a pacing trigger signal provided by digital controller/timer circuit 74 each time the escape interval times out, an externally transmitted pacing command is received or in response to other stored commands as is well known in the pacing art. By way of example, output amplifier 96 may correspond generally to an output amplifier disclosed in U.S. Pat. No. 4,476,868 to Thompson, hereby incorporated by reference in its entirety.

The specific embodiments of input amplifier 88, output amplifier 96 and EGM amplifier 94 identified herein are presented for illustrative purposes only, and are not intended to be limiting in respect of the scope of the present invention. The specific embodiments of such circuits may not be critical to practicing some embodiments of the present invention so long as they provide means for generating a stimulating pulse and are capable of providing signals indicative of natural or stimulated contractions of heart 8.

In some preferred embodiments of the present invention, IMD 10 may operate in various non-rate-responsive modes, including, but not limited to, DDD and DDI, modes. In other preferred embodiments of the present invention, IMD 10 may operate in various rate-responsive modes, including, but not limited to, DDDR, DDIR, VVIR, VOOR and VVTR modes. Some embodiments of the present invention are capable of operating in both non-rate-responsive and rate responsive modes. Moreover, in various embodiments of the present invention IMD 10 may be programmably configured to operate so that it varies the rate at which it delivers stimulating pulses to heart 8 only in response to one or more selected sensor outputs being generated. Numerous pacemaker features and functions not explicitly mentioned herein may be incorporated into IMD 10 while remaining within the scope of the present invention.

The present invention is not limited in scope to single-sensor or dual-sensor pacemakers, and is further not limited to IMDs comprising activity or pressure sensors only. Nor is the present invention limited in scope to single-chamber pacemakers, single-chamber leads for pacemakers or single-sensor or dual-sensor leads for pacemakers. Thus, various embodiments of the present invention may be practiced in conjunction with more than two leads or with multiple-chamber pacemakers, for example. At least some embodiments of the present invention may be applied equally well in the contexts of single-, dual-, triple- or quadruple-chamber pacemakers or other types of IMDs. See, for example, U.S. Pat. No. 5,800,465 to Thompson et al., hereby incorporated by reference herein in its entirety, as are all U.S. patents referenced therein.

IMD 10 may also be a pacemaker-cardioverter-defibrillator ("PCD") corresponding to any of numerous commercially available implantable PCDs. Various embodiments of the present invention may be practiced in conjunction with PCDs such as those disclosed in U.S. Pat. No. 5,545,186 to Olson et al., U.S. Pat. No. 5,354,316 to Keimel, U.S. Pat. No. 5,314,430 to Bardy, U.S. Pat. No. 5,131,388 to Pless and U.S. Pat. No. 4,821,723 to Baker et al., all of which are hereby incorporated by reference, each in their respective entireties.

Figure 4:
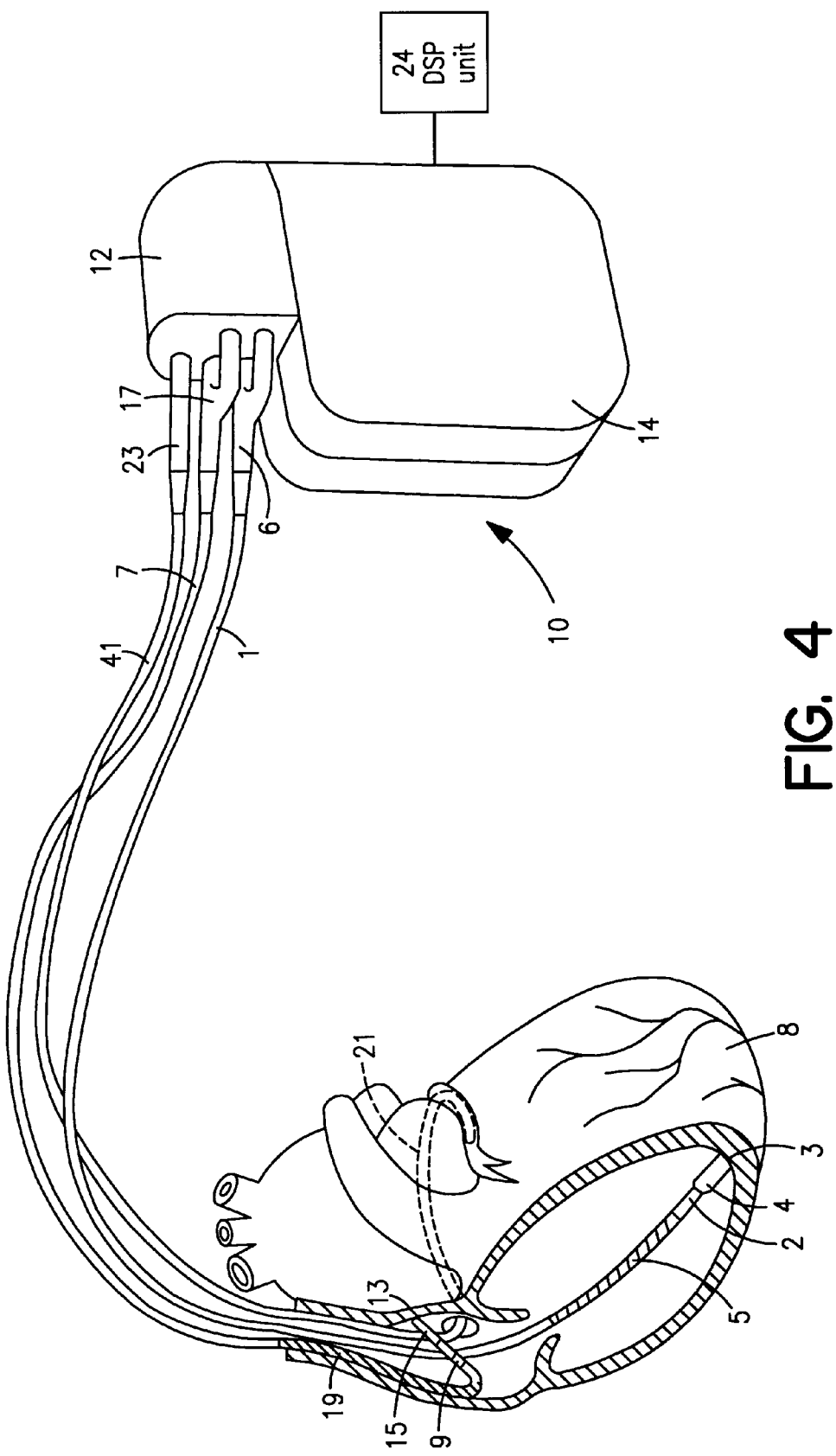
FIG. 4 is a schematic view of another embodiment of an implantable medical device, made in accordance with the present invention.
Figure 5:
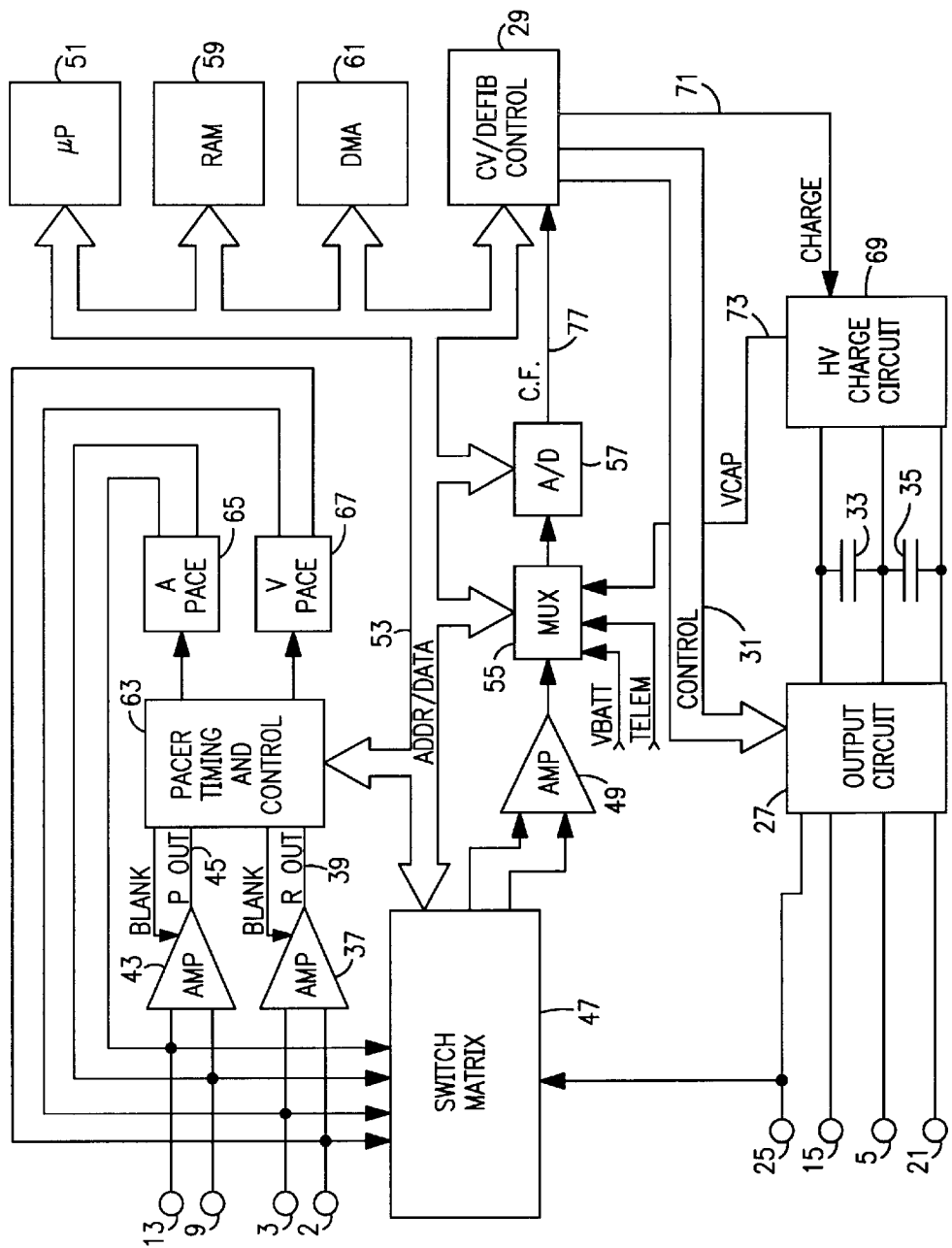
FIG. 5 is a block diagram illustrating components of an embodiment of the implantable medical device of FIG. 4, made in accordance with the present invention.

FIGS. 4 and 5 illustrate one embodiment of IMD 10 and a corresponding lead set of the present invention, where IMD 10 is a PCD. In FIG. 4, the ventricular lead takes the form of leads disclosed in the '838 and '430 patents, and includes an elongated insulative lead body 1 carrying three concentric coiled conductors separated from one another by tubular insulative sheaths. Located adjacent the distal end of lead 1 are ring electrode 2, extendable helix electrode 3 mounted retractably within insulative electrode head 4 and elongated coil electrode 5. Each of the electrodes is coupled to one of the coiled conductors within lead body 1. Electrodes 2 and 3 are employed for cardiac pacing and for sensing ventricular depolarizations. At the proximal end of the lead is bifurcated connector 6, which carries three electrical connectors, each coupled to one of the coiled conductors. Defibrillation electrode 5 may be fabricated from platinum, platinum alloy or other materials known to be usable in implantable defibrillation electrodes and may be about 5 cm in length.

The atrial/SVC lead shown in FIG. 4 includes elongated insulative lead body 7 carrying three concentric coiled conductors separated from one another by tubular insulative sheaths corresponding to the structure of the ventricular lead. Located adjacent the J-shaped distal end of the lead are ring electrode 9 and extendable helix electrode 13 mounted retractably within an insulative electrode head 15. Each of the electrodes is coupled to one of the coiled conductors within lead body 7. Electrodes 13 and 9 are employed for atrial pacing and for sensing atrial depolarizations. Elongated coil electrode 19 is provided proximal to electrode 9 and coupled to the third conductor within lead body 7. Electrode 19 preferably is 10 cm in length or greater and is configured to extend from the SVC toward the tricuspid valve. In one embodiment of the present invention, approximately 5 cm of the right atrium/SVC electrode is located in the right atrium with the remaining 5 cm located in the SVC. At the proximal end of the lead is bifurcated connector 17, which carries three electrical connectors, each coupled to one of the coiled conductors.

The coronary sinus lead shown in FIG. 4 assumes the form of a coronary sinus lead disclosed in the above cited '838 patent, and includes elongated insulative lead body 41 carrying one coiled conductor coupled to an elongated coiled defibrillation electrode 21. Electrode 21, illustrated in broken outline in FIG. 4, is located within the coronary sinus and the great vein of the heart. At the proximal end of the lead is connector plug 23 carrying an electrical connector coupled to the coiled conductor. The coronary sinus/great vein electrode 41 may be about 5 cm in length.

Implantable PCD 10 is shown in FIG. 4 in combination with leads 1, 7 and 41, and lead connector assemblies 23, 17 and 6 inserted into connector block 12. Optionally, insulation of the outward facing portion of housing 14 of PCD 10 may be provided using a plastic coating such as parylene or silicone rubber, as is employed in some unipolar cardiac pacemakers. The outward facing portion, however, may be left uninsulated or some other division between insulated and uninsulated portions may be employed. The uninsulated portion of housing 14 serves as a subcutaneous defibrillation electrode to defibrillate either the atria or ventricles. Lead configurations other that those shown in FIG. 4 may be practiced in conjunction with the present invention, such as those shown in U.S. Pat. No. 5,690,686 to Min et al., hereby incorporated by reference in its entirety.

FIG. 5 is a functional schematic diagram of one embodiment of implantable PCD 10 of the present invention. This diagram should be taken as exemplary of the type of device in which various embodiments of the present invention may be embodied, and not as limiting, as it is believed that the invention may be practiced in a wide variety of device implementations, including cardioverter and defibrillators which do not provide anti-tachycardia pacing therapies.

PCD 10 is provided with an electrode system. If the electrode configuration of FIG. 4 is employed, the correspondence to the illustrated electrodes is as follows. Electrode 25 in FIG. 5 includes the uninsulated portion of the housing of PCD 10. Electrodes 25, 15, 21 and 5 are coupled to high voltage output circuit 27, which includes high voltage switches controlled by CV/defib control logic 29 via control bus 31. Switches disposed within circuit 27 determine which electrodes are employed and which electrodes are coupled to the positive and negative terminals of the capacitor bank (which includes capacitors 33 and 35) during delivery of defibrillation pulses.

Electrodes 2 and 3 are located on or in the ventricle and are coupled to the R-wave amplifier 37, which preferably takes the form of an automatic gain controlled amplifier providing an adjustable sensing threshold as a function of the measured R-wave amplitude. A signal is generated on R-out line 39 whenever the signal sensed between electrodes 2 and 3 exceeds the present sensing threshold.

Electrodes 9 and 13 are located on or in the atrium and are coupled to the P-wave amplifier 43, which preferably also takes the form of an automatic gain controlled amplifier providing an adjustable sensing threshold as a function of the measured P-wave amplitude. A signal is generated on P-out line 45 whenever the signal sensed between electrodes 9 and 13 exceeds the present sensing threshold. The general operation of R-wave and P-wave amplifiers 37 and 43 may correspond to that disclosed in U.S. Pat. No. 5,117,824, by Keimel et al., issued Jun. 2, 1992, for "An Apparatus for Monitoring Electrical Physiologic Signals," hereby incorporated by reference in its entirety.

Switch matrix 47 is used to select which of the available electrodes are coupled to wide band (0.5–200 Hz) amplifier 49 for use in digital signal analysis. Selection of electrodes is controlled by the microprocessor 51 via data/address bus 53, which selections may be varied as desired. Signals from the electrodes selected for coupling to bandpass amplifier 49 are provided to multiplexer 55, and thereafter converted to multi-bit digital signals by A/D converter 57, for storage in RAM (memory) 59 under control of direct memory access circuit 61. Microprocessor 51 may employ digital signal analysis techniques to characterize the digitized signals stored in RAM (memory) 59 to recognize and classify the patient's heart rhythm employing any of the numerous signal-processing methodologies known to the art.

The remainder of the circuitry is dedicated to the provision of cardiac pacing, cardioversion and defibrillation therapies, and, for purposes of the present invention, may correspond to circuitry known to those skilled in the art. The following exemplary apparatus is disclosed for accomplishing pacing, cardioversion and defibrillation functions. Pacer timing/control circuitry 63 preferably includes programmable digital counters which control the basic time intervals associated with DDD, VVI, DVI, VDD, AAI, DDI and other modes of single and dual chamber pacing well known to the art. Circuitry 63 also preferably controls escape intervals associated with anti-tachyarrhythmia pacing in both the atrium and the ventricle, employing any anti-tachyarrhythmia pacing therapies known to the art.

Intervals defined by pacing circuitry 63 include atrial and ventricular pacing escape intervals, the refractory periods during which sensed P-waves and R-waves are ineffective to restart timing of the escape intervals and the pulse widths of the pacing pulses. The durations of these intervals are determined by microprocessor 51, in response to stored data in RAM (memory) 59 and are communicated to pacing circuitry 63 via address/data bus 53. Pacer circuitry 63 also determines the amplitude of the cardiac pacing pulses under control of microprocessor 51.

During pacing, escape interval counters within pacer timing/control circuitry 63 are reset upon sensing of R-waves and P-waves as indicated by signals on lines 39 and 45, and in accordance with the selected mode of pacing on time-out trigger generation of pacing pulses by pacer output circuitry 65 and 67, which are coupled to electrodes 9, 13, 2 and 3. Escape interval counters are also reset on the generation of pacing pulses and thereby control the basic timing of cardiac pacing functions, including anti-tachyarrhythmia pacing. The durations of the intervals defined by escape interval timers are determined by microprocessor 51 via data/address bus 53. The value of the count present in the escape interval counters when reset by sensed R-waves and P-waves may be used to measure the durations of R-R intervals, P-P intervals, P-R intervals and R-P intervals, which measurements are stored in RAM (memory) 59 and used to detect the presence of tachyarrhythmias.

Microprocessor 51 most preferably operates as an interrupt driven device, and is responsive to interrupts from pacer timing/control circuitry 63 corresponding to the occurrence of sensed P-waves and R-waves and corresponding to the generation of cardiac pacing pulses. Those interrupts are provided via data/address bus 53. Any necessary mathematical calculations to be performed by microprocessor 51 and any updating of the values or intervals controlled by pacer timing/control circuitry 63 take place following such interrupts.

Detection of atrial or ventricular tachyarrhythmias, as employed in the present invention, may correspond to any of the various tachyarrhythmia detection algorithms presently known in the art. For example, the presence of an atrial or ventricular tachyarrhythmia may be confirmed by detecting a sustained series of short R-R or P-P intervals of an average rate indicative of tachyarrhythmia or an unbroken series of short R-R or P-P intervals. The suddenness of onset of the detected high rates, the stability of the high rates, and a number of other factors known in the art may also be measured at this time. Appropriate ventricular tachyarrhythmia detection methodologies measuring such factors are described in U.S. Pat. No. 4,726,380 issued to Vollmann, U.S. Pat. No. 4,880,005, issued to Pless et al. and U.S. Pat. No. 4,830,006, issued to Haluska et al., all hereby incorporated by reference, each in their respective entirety. An additional set of tachycardia recognition methodologies is disclosed in the article "Onset and Stability for Ventricular Tachyarrhythmia Detection in an Implantable Pacer-Cardioverter-Defibrillator" by Olson et al., published in Computers in Cardiology, Oct. 7–10, 1986, *IEEE Computer Society Press,* pp. 167–170, also hereby incorporated by reference in its entirety. Atrial fibrillation detection methodologies are disclosed in published PCT Application Ser. No. US92/02829, Publication No. WO92/18198, by Adams et al., and in the article "Automatic Tachycardia Recognition", by Arzbaecher et al., published in *PACE,* May-June, 1984, pp. 541–547, both of which are hereby incorporated by reference in their entireties.

In the event an atrial or ventricular tachyarrhythmia is detected and an anti-tachyarrhythmia pacing regimen is desired, appropriate timing intervals for controlling generation of anti-tachyarrhythmia pacing therapies are loaded from microprocessor 51 into the pacer timing and control circuitry 63, to control the operation of the escape interval counters therein and to define refractory periods during which detection of R-waves and P-waves is ineffective to restart the escape interval counters.

Alternatively, circuitry for controlling the timing and generation of anti-tachycardia pacing pulses as described in U.S. Pat. No. 4,577,633, issued to Berkovits et al. on Mar. 25, 1986, U.S. Pat. No. 4,880,005, issued to Pless et al. on Nov. 14, 1989, U.S. Pat. No. 4,726,380, issued to Vollmann et al. on Feb. 23, 1988 and U.S. Pat. No. 4,587,970, issued to Holley et al. on May 13, 1986, all of which are hereby incorporated by reference in their entireties, may also be employed.

In the event that the generation of a cardioversion or defibrillation pulse is required, microprocessor 51 may employ an escape interval counter to control timing of such cardioversion and defibrillation pulses, as well as the associated refractory periods. In response to the detection of atrial or ventricular fibrillation or tachyarrhythmia requiring a cardioversion pulse, microprocessor 51 activates cardioversion/defibrillation control circuitry 29, which initiates charging of the high voltage capacitors 33 and 35 via charging circuit 69, under the control of high voltage charging control line 71. The voltage on the high voltage capacitors is monitored via VCAP line 73, which is passed through multiplexer 55 and in response to reaching a predetermined value set by microprocessor 51, results in generation of a logic signal on Cap Full (CF) line 77 to terminate charging. Thereafter, timing of the delivery of the defibrillation or cardioversion pulse is controlled by pacer timing/control circuitry 63. Following delivery of the fibrillation or tachycardia therapy, microprocessor 51 returns the device to a cardiac pacing mode and awaits the next successive interrupt due to pacing or the occurrence of a sensed atrial or ventricular depolarization.

Several embodiments of appropriate systems for the delivery and synchronization of ventricular cardioversion and defibrillation pulses and for controlling the timing functions related to them are disclosed in U.S. Pat. No. 5,188,105 to Keimel, U.S. Pat. No. 5,269,298 to Adams et al. and U.S. Pat. No. 4,316,472 to Mirowski et al., all of which are hereby incorporated by reference, each in its respective entirety. Any known cardioversion or defibrillation pulse control circuitry is believed to be usable in conjunction with various embodiments of the present invention, however. For example, circuitry controlling the timing and generation of cardioversion and defibrillation pulses such as that disclosed in U.S. Pat. No. 4,384,585 to Zipes, U.S. Pat. No. 4,949,719 to Pless et al., or U.S. Pat. No. 4,375,817 to Engle et al., all of which are hereby incorporated by reference in their entireties, may also be employed.

Continuing to refer to FIG. 5, delivery of cardioversion or defibrillation pulses may be accomplished by output circuit 27 under the control of control circuitry 29 via control bus 31. Output circuit 27 determines whether a monophasic or biphasic pulse is delivered, the polarity of the electrodes and which electrodes are involved in delivery of the pulse. Output circuit 27 also includes high voltage switches, which control whether electrodes are coupled together during delivery of the pulse. Alternatively, electrodes intended to be coupled together during the pulse may simply be permanently coupled to one another, either exterior to or within the interior of the device housing, and polarity may similarly be pre-set, as in current implantable defibrillators. An example of output circuitry for delivery of biphasic pulse regimens to multiple electrode systems may be found in U.S. Pat. No. 4,953,551, issued to Mehra, and in U.S. Pat. No. 4,727,877, both of which are hereby incorporated by reference in their entireties.

An example of circuitry that may be used to control delivery of monophasic pulses is disclosed in U.S. Pat. No. 5,163,427 to Keimel, also hereby incorporated by reference in its entirety. Output control circuitry similar to that disclosed in the '551 patent or in U.S. Pat. No. 4,800,883 to Winstrom, which is hereby incorporated by reference in its entirety, may also be used in conjunction with various embodiments of the present invention to deliver biphasic pulses.

Alternatively, IMD 10 may be an implantable nerve stimulator or muscle stimulator, such as that disclosed in U.S. Pat. No. 5,199,428 to Obel et al., U.S. Pat. No. 5,207,218 to Carpentier et al. or U.S. Pat. No. 5,330,507 to Schwartz, or an implantable monitoring device such as that disclosed in U.S. Pat. No. 5,331,966 issued to Bennet et al., all of which are hereby incorporated by reference, each in their respective entireties. The present invention is believed to find wide application to any form of implantable electrical device for use in conjunction with electrical leads.

Alternatively, IMD 10 may be an implantable device with no leads. For example, IMD 10 may be an implantable device having no leads but having electrodes on its surface that may be used to monitor a patient's heart signals over a long period of time. Upon a "trigger" event, the device 10 amplifies the signals related to voltage differences measured between its electrodes. These signals may be digitized and stored in internal memory. These signals may be compressed in accordance with the present invention prior to storage.

Figure 6:
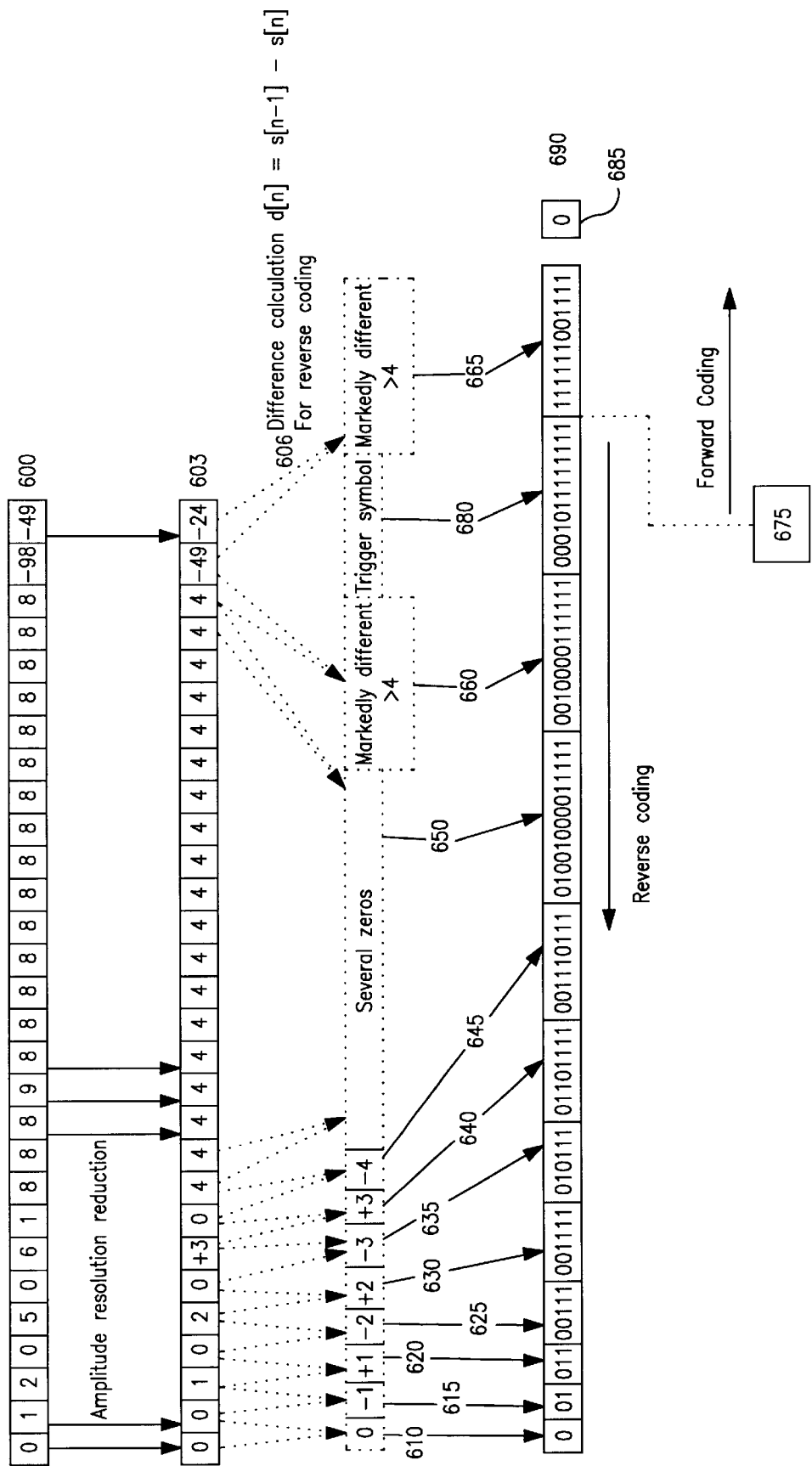
FIG. 6 is a schematic representation of the compression of a data stream in accordance with one embodiment of the present invention.

FIG. 6 shows a schematic representation of a data stream being compressed in accordance with the present invention at 600. Although only one data stream is shown, any suitable number of data streams may be compressed in accordance with the present invention.

In one embodiment of the invention, data stream 600 is a digital data stream. Data stream 600 may represent one or a series of cardiac signals. Data stream 600 may also represent a processed version of one or a series of cardiac signals. Data stream 600 may be generated by any suitable means such as, for example, the circuitry of device 10. In one embodiment of the invention, data stream 600 is generated by a digital signal processor as described above. For example, in one embodiment of the invention, data stream 600 is generated according to the methods and systems disclosed in U.S. Pat. No. 6,029,087 to Wohlgemuth, herein incorporated by reference in its entirety.

Data stream 600 may also comprise input received by any suitable means such as, for example cardiac input received by device 10. Data stream 600 may also be compressed for storage in any suitable memory location of device 10, including but not limited to a location in memory 59 and/or RAM 68.

Data stream 600 may be compressed using any suitable means. For example, data stream 600 may be compressed using processor 64 of device 10. Alternatively, data stream 600 may be compressed by means of a special circuit dedicated to performing this compression function. In one embodiment of the invention, compression of data stream 600 may be accomplished using any suitable compression algorithm that compresses 8-bit values into variable size and sample rate data. Other suitable compression algorithms which compress values of any suitable size, including, but not limited to 2-bit, 6-bit, 10-bit, 16-bit, 32-bit, etc., may be used. Suitable compression algorithms may compress any size values into variable size and sample rate data.

Data stream 600 may comprise a plurality of data values. For example, the values (separated by commas) indicated in 600 are 0, 1, 2, 0, 5, 0, 6, 1, 8, 8, 8, 9, 8, 8,8, 8, 8, 8, 8, 8, 8, 8, 8, 8, 8, 8, 8, −98, −49

Compression of data stream 600 may be accomplished by first reducing the amplitude resolution of the data stream. In one embodiment of the invention, the amplitude resolution reduction is accomplished by dividing the values of data stream 600 by a number that is a constant. In a preferred embodiment of the invention, the values of data stream 600 are divided by a number that is a constant and a power of 2, for example $2^1=2$. Alternatively, any suitable constant may be used, including, but not limited to, three or a power of 3, five or a power of 5, etc. This amplitude resolution reduction results in a data stream with reduced amplitude resolution 603. In one embodiment of the invention, the values may not require amplitude resolution reduction and the difference calculations made at 606 may be based on data stream 600 without the amplitude resolution reduction step.

In the embodiment shown in FIG. 6, data stream 600 is reduced to data stream 603 and, from this data stream 603 difference calculations are made at 606 by taking the difference between subsequent data values in data stream 603.

Data stream 603 may comprise a plurality of data values. For example, the values (separated by commas) indicated in 603 are 0, 0, 1, 0, 2, 0, 3, 0, 4, 4, 4, 4, 4, 4, 4, 4, 4, 4, 4, 4, 4, 4, 4, 4, 4, −49, −24

In the embodiment shown in FIG. 6, these values are a result of the amplitude resolution reduction of data stream 600.

Conversion may then be completed based on the determined difference. The difference calculation of data stream 603 resulting in bit stream 690 may be accomplished by determining a value of the current sample and determining a difference between the value of the current sample and a value of the previous data sample. In one embodiment of the invention, conversion occurs in a first, or forward direction of data streams 603, 690 (i.e., forward encoding). During forward encoding, the value of the current sample s[n] and the value of the previous sample s[n−1] are determined and the difference d[n] is calculated between the current sample s[n] and the previous sample s[n−1], i.e., $d[n]=s[n]-s[n-1]$.

In one embodiment of the invention, the difference signal has less variance than the value of the current sample. The difference signal may thus be more efficiently encoded using entropy encoding than the value of the current sample.

Alternatively, as seen in FIG. 6, conversion may occur in a second, or reverse direction of data streams 603, 690 (i.e., reverse encoding). During reverse encoding, the value of the previous sample s[n−1] and the value of the current sample s[n] are determined and the difference d[n] is calculated between the previous sample s[n−1] and the current sample s[n], i.e., $d[n]=s[n-1]-s[n]$.

Difference calculation applied to data stream 603 may be represented by a series of difference calculations shown at 606. For example, the values (separated by commas) indicated in the calculations shown at 606 are a difference of 0, a difference of −1, a difference of +1, a difference of −2, a difference of +2, a difference of −3, a difference of +3, a difference of −4, a series of differences of 0, a markedly different difference (i.e. greater than or equal to 4 or less than or equal to 5), a unique bit pattern trigger symbol. A markedly different difference.

The next step in the conversion process is to translate the calculated differences to compressed bit patterns or sequences of compressed bit patterns, according to a set of rules.

In one embodiment of the invention, these bit patterns are selected such that when they are concatenated to a serial bit stream for example stream 690, each compressed bit pattern can be uniquely identified when decoding the serial bit stream in a certain direction. Decoding the bit stream in the opposite direction will yield ambiguous or erroneous results.

The way the compressed bit patterns or sequences of compressed bit patterns are concatenated depends on the set of compressed bit patterns and the direction of encoding, which in its turn depends on the direction of decoding. If, for example, the set of compressed bit patterns is uniquely identifiable when processed from the left (most significant) bit to the right (least significant) bit, and decoding starts at the start of the serial bit stream. In this embodiment, forward encoding may be used, and the compressed bit patterns or sequences of compressed bit patterns may be concatenated starting with the left (most significant) bit, which, if it is not the first compressed bit pattern in the serial bit stream, is concatenated to the right (least significant) bit of its predecessor in the serial bit stream. If, however, the decoding starts at the end of the serial bit stream, and the same set of compressed bit patterns is used, the compressed bit patterns may be mirrored before concatenating, such that the right (least significant) bit is concatenated to the left (most significant) bit of its predecessor in the serial bit stream.

In another embodiment of the invention, the serial bit stream 690 may be further processed. For example, serial bit stream 690 may be formatted in a serial stream of bytes or words or may by formatted in any suitable manner for storage such as in a storage location of IMD 10, including but not limited to, a location of memory 59 and/or RAM 68.

As seen in FIG. 6, the serial bit pattern 690 may be created by assigning a bit pattern to the difference calculated between the current sample and the previous sample. Translation of several bit patterns may result in a serial bit stream such as bit stream 690. For example, a bit pattern may be assigned to the difference using the following rules of conversion:

1. If the difference is 0, then its compressed bit pattern is 0
2. If the difference is 1 less than the previous value, its compressed bit pattern is 10
3. If the difference is 1 more than the previous value, its compressed bit pattern is 110
4. If the difference is 2 less than the previous value, its compressed bit pattern is 1110 followed by bit pattern 0
5. If the difference is 2 more than the previous value, its compressed bit pattern is 11110, followed by bit pattern 0
6. If the difference is 3 less than the previous value, its compressed bit pattern is 1110 followed by bit pattern 10
7. If the difference is 3 more than the previous value, its compressed bit pattern is 11110 followed by bit pattern 110
8. If the difference is 4 less than the previous value, its compressed bit pattern is 1110 1110 followed by bit pattern 0
9. If the difference values comprise a sequence of more than 14 0's (zeros), the sequence of zeros is represented by one compressed bit pattern that is build from bit pattern 111110 followed by an 8-bit binary value of the number of sequential 0's (thus, if there are x zeros, the 8-bit binary value equals x)
10. If the difference is markedly different from the previous value, its compressed bit pattern is 111111 followed by the 7-bit binary value of the current reduced resolution data sample. Due to the fact that this compressed bit pattern does not contain a difference value, but contains a sample value directly related to a sample value of the original data stream, this specific code may also be referred to as absolute signal value code. In one embodiment of the invention, the decision whether a sample is markedly different from a previous sample may be determined by the length of the bit pattern that is generated when a current sample value differs from the previous sample value by a factor of 2.

i.e., for differences greater than zero (>0) the general equation may be (Sample value difference/2)*$a$+$b$>$c$→Markedly different where a=the number of bits required to code a two symbol; b=the number of bits required to code one (1); and c=the number of bits required to code the actual value of the current sample For example, in the embodiment shown in FIG. 6, for differences greater than zero (>0), the equation may be written (Sample value difference/2)*5+3>13→Markedly different where a=5, b=3 and c=13 this may be translated to

13<(Sample value difference/2)*5+3 and may also be written as

13<2, 5*Sample value difference+3 the 3 may be moved to the other side of the equation to get

13−3<2,5*Sample value difference which equals

10<2,5*Sample value difference by switching the direction of the equation, the above may be written Sample value difference>(10/2,5)

which results in

Sample value difference>4

This results in the embodiment shown in FIG. 6 at 660 where a markedly different value is a sample value difference greater than or equal to four (>/=4).

Again, in the embodiment shown in FIG. 6, for differences less than zero (<0), the general equation may be written (Sample value difference/2)*$a$+$b$>$c$→Markedly different where a=the number of bits required to code a minus two symbol; b=the number of bits required to code minus one (−1); and c=the number of bits required to code the actual value of the current sample For example, in the embodiment shown in FIG. 6, for differences less than zero (>0), the equation may be written (Sample value difference/2)*4+2>13→Markedly different where a=4, b=2 and c=13 this may be translated to

13<(Sample value difference/2)*4+2 and may also be written as

13<2, 4*Sample value difference+2 the 2 may be moved to the other side of the equation to get

13−2<2,4*Sample value difference which equals

11<2,4*Sample value difference by switching the direction of the equation, the above may be written Sample value difference>11/2, 4 which results in

Sample value difference>5,5 which, because the difference involved negative whole numbers, may further be translated to Sample value difference<−5

This results in another embodiment shown in FIG. 6 at 665 where a markedly different value is a sample value difference less than or equal to negative five (</=−5).

It is to be understood that the rules described above are only one set of possible rules for use in accordance with the present invention. The choice of the symbol set and the choice of which symbols map to which bit pattern may dictate a different set of rules which are still contemplated by the present invention. For example, a larger symbol set is imaginable, including, but not limited to a set which provides a compressed bit pattern for difference values that are equal to 6, equal to −6, equal to 7, equal to −7, etc. A different symbol set will comprise different corresponding bit patterns and will also provide different criteria for whether a difference value is "markedly different."

Thus, as seen in the embodiment shown in FIG. 6, at 610, the difference value is 0, so its compressed bit pattern is 0.

At 615, the difference value is −1, so its compressed bit pattern is 10. Because FIG. 6 illustrates reverse coding, the mirror image of the compressed bit pattern, 01, is shown in FIG. 6.

At 620, the difference value is 1, so its compressed bit pattern is 110. Because FIG. 6 illustrates reverse coding, the mirror image of the compressed bit pattern, 011, is shown in FIG. 6.

At 625, the difference value is −2, so its compressed bit pattern is 11100. Because FIG. 6 illustrates reverse coding, the mirror image of the compressed bit pattern, 00111, is shown in FIG. 6.

At 630, the difference value is 2, so its compressed bit pattern is 111100. Because FIG. 6 illustrates reverse coding, the mirror image of the compressed bit pattern, 001111, is shown in FIG. 6.

At 635, the difference value is −3, so its compressed bit pattern is 111010. Because FIG. 6 illustrates reverse coding, the mirror image of the compressed bit pattern 010111 is shown in FIG. 6.

At 640, the difference value is 3, so its compressed bit pattern is 11110110. Because FIG. 6 illustrates reverse coding, the mirror image of the compressed bit pattern 01101111 is shown in FIG. 6.

At 645, the difference value is −4, so its compressed bit pattern is 111011100. Because FIG. 6 illustrates reverse coding, the mirror image of the compressed bit pattern, 001110111, is shown in FIG. 6.

At 650, the difference values turns out to be a 0 several consecutive times. Each difference value of zero in this series generates a compressed bit pattern of zero, resting in a sequence of more than 14 zeroes in the compressed data stream. In such a case, rather than incorporating the sequence of zeroes into the data stream as a series of 0 compressed bit patterns, the sequence of zeroes may be represented by the bit pattern 111110 followed by an 8-bit binary value of the number of sequential zeros (i.e., if there are x zeros, the 8-bit binary value equals x). Alternatively, this bit pattern may be followed by any appropriate binary representation of the number of sequential zeroes, including but not limited to a 6-bit binary value, a 10-bit binary value, a 16-bit binary value and a 32-bit binary value. In the embodiment of FIG. 6, the series of zeroes has a compressed bit pattern of 11111000010010. Because FIG. 6 illustrates reverse coding, the mirror image of the compressed bit pattern, 01001000011111, is shown in FIG. 6.

At 660, the difference value of 53 is a large deflection value. The difference value 53 results from the calculation (s[n−1]=4) minus (s[n]=−49). This large difference value may indicate that the value of the current data sample is markedly different from the value of the previous data sample. So its compressed bit pattern is determined in the following manner. Instead of the difference data stream value 53, the value of the previous reduced resolution data sample (i.e., 4) is converted to a 7-bit binary value, which is 0000100. Then, 111111 is inserted before the 7-bit binary value, i.e., before 0000100, resulting in a compressed bit pattern of 1111110000100. Because FIG. 6 illustrates reverse coding, the mirror image of the compressed bit pattern, 0010000111111, is shown in FIG. 6.

As described above, this compressed bit pattern does not contain a difference value, but contains a sample value (0000100) which is directly related to a sample value (4) of the original data stream. This specific compressed bit pattern may thus, also be referred to as absolute signal value code.

In some embodiments of the invention, the absolute signal value codes may also be compressed bit patterns that store the actual differences (not shown). Thus, the compressed bit pattern for the difference between current sample value −49 and previous sample value 4, i.e., for 53 may also be stored. The compressed bit code would then consist of an identifying bit pattern, for example, 111111 followed by the markedly different difference value, which in the case of current sample value of −49 and a previous sample value of 4, would be 53.

At 665, the difference value of 25 is also a large deflection value. Because at 665 there has been a switch from reverse to forward coding, the difference value 25 results from the calculation of (s[n]=−24) minus (s[n−1]=−49).

This large difference value may indicate that the value of the current data sample is markedly different from the value of the previous data sample. So its compressed bit pattern is determined in the following manner. Instead of the difference data stream value 25, the value of the previous reduced resolution data sample (i.e., −49) is converted to a 7-bit binary value, which is 1001111. Then, 111111 is inserted before the 7-bit binary value, i.e., before 1001111, resulting in a compressed bit pattern of 1111111001111. Because the switch to forward coding has now occurred in FIG. 6 the actual compressed bit pattern determined above is shown in FIG. 6.

As described above, this compressed bit pattern does not contain a difference value, but contains a sample value (1001111) which is directly related to a sample value (−49) of the original data stream. This specific compressed bit pattern may thus, also be referred to as absolute signal value code. Alternatively, as described above, the compressed bit pattern may contain the markedly different difference value.

The application of the above rules results in a compressed data stream such as that shown at 690 in FIG. 6. Compression may continue in this manner as long as data samples are being received, for example, from data stream 600.

Alternatively, compression may continue in this manner until a trigger symbol 680 is encoded. The trigger symbol may be a component of the compressed data stream as indicated at 680. Alternatively, an external trigger symbol 675 may be stored in another location external to the data stream, such as a storage location of IMD 10, including but not limited to, a location of memory 59, and/or RAM 68. Trigger symbol 675, 680 may be a uniquely identifiable bit pattern that is distinguishable from the bit patterns derived according to the rules described above.

When a trigger event occurs (as discussed further below), trigger symbol 680 may be inserted into bit stream 690. Alternatively, when a trigger event occurs, the point in the bit stream where the trigger occurred maybe stored at an external location 675. Upon the occurrence of a trigger event, the compression algorithm may switch from reverse to forward encoding. This switch enables the compression algorithm to continue generation of data until the available storage space runs out. Alternatively, the compression algorithm may switch from forward to reverse encoding when a trigger event occurs. Thus, during decoding, trigger symbol 675, 680 may indicate that such a reversal of the encoding direction of the compression algorithm occurred during encoding. Furthermore, trigger symbol 675, 680 may indicate that a trigger event occurred during encoding.

Alternatively, compression may continue in this manner until an absolute reference value 685 is encoded into bit stream 690. For example, the absolute reference value 685 may be encoded into bit stream 690 at the end of the data stream 690. The absolute reference value 685 may be used as a reference point. Absolute reference value 685 may indicate for example, the starting point of bit stream 690 or the ending point of bit stream 690. For example, in one embodiment of the invention, the absolute reference value 685 of compressed data stream 690, may be a zero (0). Alternatively the absolute reference value 685 of compressed data stream 690 may be a one (1). Alternatively, the absolute reference value 685 may be the difference between the last processed sample from reduced amplitude resolution signal data stream 603 and the absolute value zero (0). Alternatively, the absolute reference value may be any suitable value for identifying compressed data stream 690.

In another embodiment of the invention, compression may continue according to the compression algorithm until a trigger symbol 675, 680 is encoded and may still continue until an absolute reference value 685 is encoded into bit stream 690.

FIGS. 7a–7f are schematic representation of various data streams encoded in accordance with the present invention. In the embodiments shown in FIGS. 7a–7f, one or more absolute signal values 660, 665 are located within the bit stream 690. Such absolute signal values 660, 665 nearby a trigger symbol may be used to reconstruct data stream 603. That is, because the bit patterns of absolute signal values 660, 665 encode an actual value from data stream 603, the value may be used to determine the other values.

For example, because the compressed bit pattern of absolute signal value 665 in the example of FIG. 6 includes the actual value –24, the value of –24 may then be reconstructed during decoding. Then because a trigger symbol 680 is encountered, the values following the trigger symbol will be reconstructed based on a switch in the encoding direction (in this case, the switch is to reverse decoding and the mirror image bit patterns will be reconstructed to actual values). Then because the compressed bit pattern of absolute signal value 660 in the example of FIG. 6 includes the actual value –49, the values of –24 and –49 may then be reconstructed in their appropriate order. The compressed bit pattern of absolute signal value 655 includes the actual value 4, so the values of –24, –49 and 4 may then be reconstructed in their appropriate order. Then because the difference value indicated at 650 indicates that there is 0 difference between the actual value 4 and the value preceding it, the values of –24, –49, 4, and 4 may then be reconstructed in their appropriate order. Furthermore, the difference value indicated at 650 indicates that there is a series of nineteen actual values of 4. So the values of –24, –49, nineteen 4s may then be reconstructed appropriately. Then the difference value indicated at 645 indicates that there is –4 difference between the actual value 4 and the value preceding it so the values of –24, –49, nineteen 4s and 0 may then be reconstructed appropriately. Reconstruction based on the stored difference values may continue in this manner until bit stream 690 is completely decoded.

Bit stream 690 may also include absolute reference values 685 as described above which may indicate the beginning or end of bit stream 690.

Absolute signal values may also occur in any suitable place in bit stream 690 in addition to occurring nearby trigger symbols or at the beginning or end of bit stream 690. Absolute signal values may also correspond, for example, to a moment or moments of "markedly different" values as described in detail above. These values may be, for example, heart signal values as previously described. These heart signal values may correspond, in turn, to values of events of interest, such as PACs, PVCs, etc.

In the embodiments shown in FIGS. 7a–7f, one or more trigger symbols 675, 680 or other trigger indicators 695 may also be associated with the bit stream 690. Trigger symbols and other such indicators 695 may correspond to a moment or moments at which a significant signal value occurs. Such signal values of interest may be, for example, PACs, PVCs, or indicators of the onset of AF.

The attending physician may preprogram parameters indicating which signal values may be considered trigger events and may thus merit the incorporation of a trigger symbol into the data stream to indicate the occurrence of such a trigger event. Alternatively, trigger events may be automatically selected from a database or lookup table or determined by IMD 10 based on information gathered by IMD 10 or on preset parameters. In one embodiment of the invention, the patient may be equipped with a trigger switch that may be applied to IMD 10 manually by the patient when the patient wishes to indicate a trigger event. For example, the patient may be equipped with a magnet and, upon sensing an event which the patient would like to indicate as a trigger event, the patient may apply the magnet to IMD 10. The signal value at the moment indicated by the patient will then be marked with a trigger symbol or other such trigger indicator in the bit stream 690. Preferably, the trigger symbol is a unique bit pattern and does not actually code the signal value, although in at least some embodiments of the invention, it is contemplated that the trigger symbol pattern could be a representation of the signal value associated with the trigger event. Most preferably, the trigger symbol indicates that the signal value associated with the trigger event follows or precedes the location of the trigger symbol in the bit stream 690. For example, in FIG. 6, trigger symbol 680 may serve to indicate that the absolute signal values stored nearby in the bit stream at 660, 665 may be indicative of trigger events or otherwise significant values. In addition, as indicated above, trigger symbol 680 may indicate the point at which the switch from reverse to forward coding occurs.

Figure 7A:
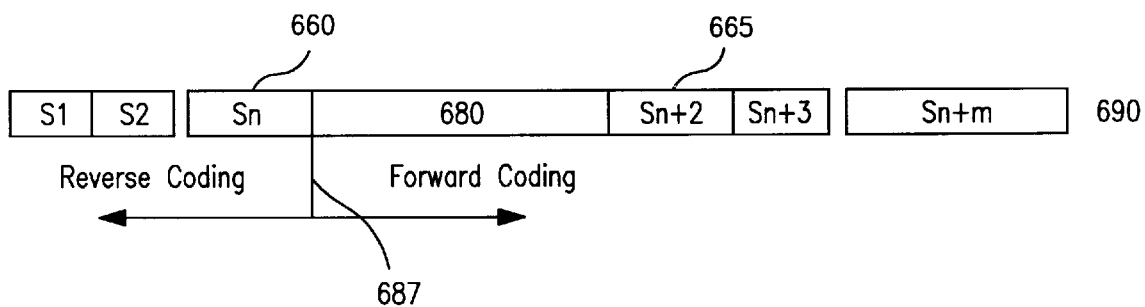
FIGS. 7a–7f are schematic representation of various data streams encoded in accordance with the present invention.
Figure 7B:
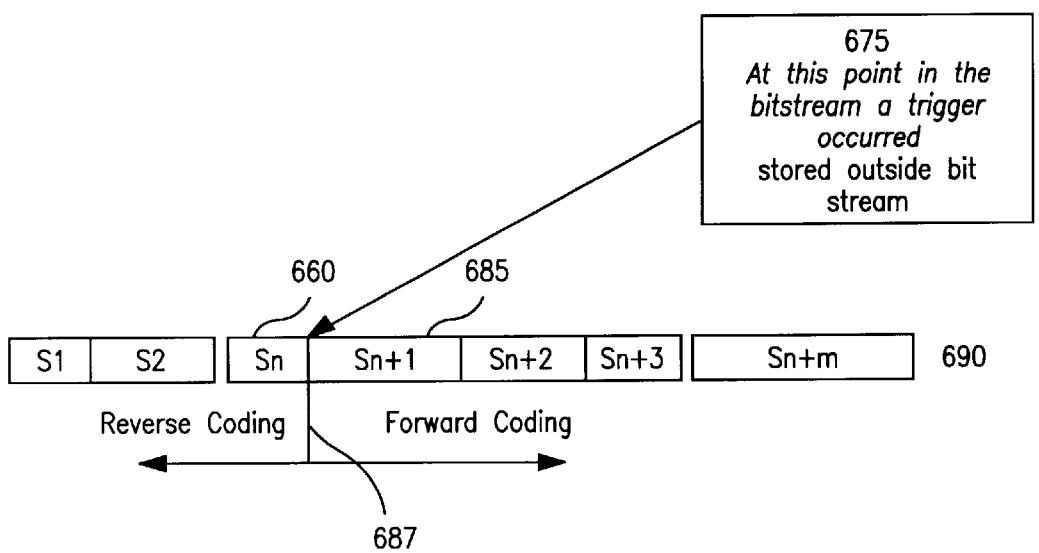
Figure 7C:
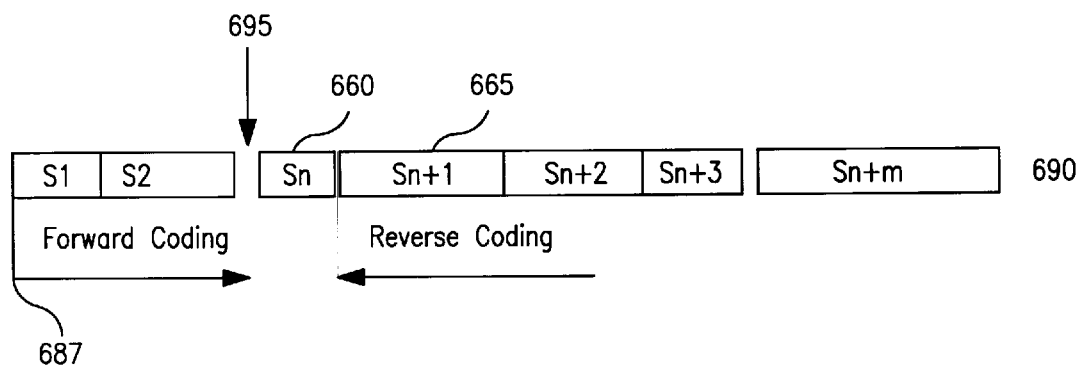

In the embodiments shown in FIGS. 7a–7c, the bit stream 690 is stored in a circular buffer. Thus data is stored continuously and newer data may overwrite the oldest data.

In FIG. 7a, trigger symbol 680 is a unique bit pattern within the bit stream 690. Trigger symbol 680 is unique whether reverse coded or forward coded. Trigger symbol 680 may indicate the moment in bit stream 690 where encoding changes from a reverse direction to a forward direction or vice versa. Bit stream 690 may also include an absolute signal value 660 which encodes an actual signal value. Alternatively, bit stream 690 may include an absolute signal value 665 which also encodes an actual signal value. Upon reaching trigger symbol 680 in bit stream 690, reverse decoding switches to a forward coding direction as indicated at 687.

In FIG. 7b, trigger symbol 675 is a unique pointer external to bit stream 690. Trigger symbol 675 may be, for example, a unique bit pattern. Trigger symbol 675 may also be any suitable pointer external to bit stream 690 which may indicate a point in bit stream 690 where encoding changes from a reverse direction to a forward direction or vice versa. Trigger symbol 675 points out that "at this point in bit stream 690, a trigger occurred". Bit stream 690 may also include an absolute signal value 660 which encodes an actual value of a signal from data stream 603. Alternatively, bit stream 690 may also include one or more other absolute signal values 665 which also encode actual values of signals. Upon reaching the point in bit stream 690 externally indicated by trigger symbol 675, reverse coding switches to a forward coding direction as indicated at 687.

In FIG. 7c, an embodiment is shown in which a trigger indicator 695 that is not a symbol indicates the occurrence of a trigger event.

Forward decoding begins at 687. At the point in bit stream 690 when trigger indicator 695 occurs, forward decoding fails. The inability to further decode the bit stream may serve to indicate that a trigger has occurred at 695. In addition, reverse decoding starts at 685 in the direction of 885. At the point in bit stream 690 when trigger indicator 695 occurs, reverse decoding fails. The combination of the locations where both forward and reverse decoding fail in bit stream 690 serve to indicate that a trigger has occurred at 695.

Figure 7D:
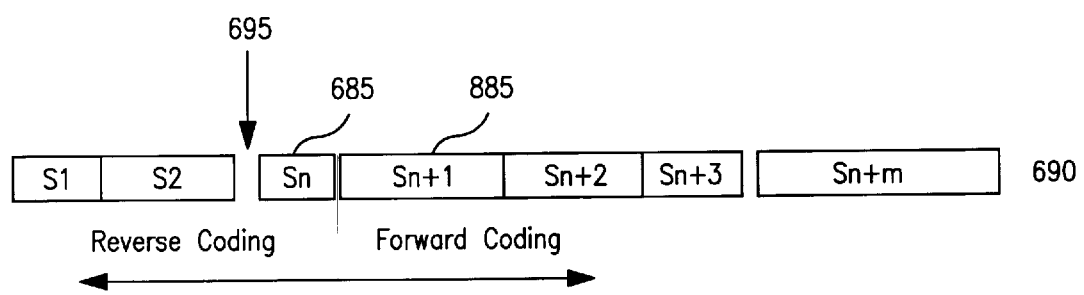

In FIG. 7d, another embodiment is shown in which a trigger indicator 695 that is not a symbol indicates the occurrence of a trigger event. Only from the point in the bit stream 690 when trigger indicator 695 occurs is it possible to fully decode bit stream 690 starting at 695 back towards the beginning using reverse decoding and towards the end using forward decoding.

Thus, in FIG. 7d, reverse decoding begins with absolute reference value 685 and may continue to the beginning of bit stream 690 whereas forward decoding begins with absolute reference value 885 and may continue till the end of bit stream 690. Only from point 695 it is possible to fully decode towards the beginning and end of bit stream 690.

Since the ability to be able to decode right back to the beginning of 690 is required in order to locate the trigger moment, this embodiment of implicit storage of the trigger moment does not make use of an circular buffer.

Figure 7E:
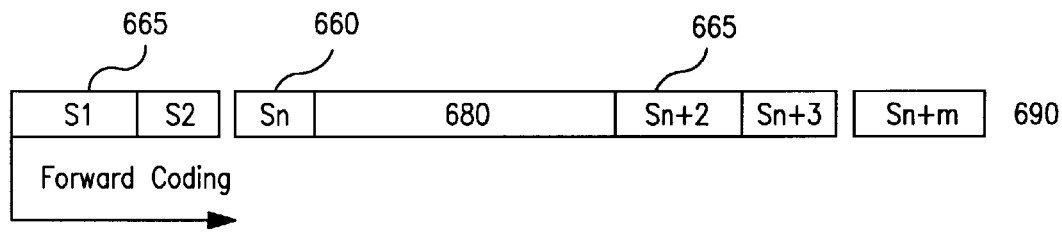

In FIG. 7e, trigger symbol 680 is a unique bit pattern within the bit stream 690. Trigger symbol 680 is unique whether reverse coded or forward coded. Trigger symbol 680 may indicate a point in the bit stream where a significant value corresponding to a significant, or trigger event, as described above, is stored. Bit stream 690 may also include an absolute reference value 685 which indicates the start of the bit stream.

In the embodiment shown in FIG. 7e, forward coding is occurring beginning at absolute reference value 685. Trigger symbol 680 in bit stream 690 may serve to indicate that absolute signal values 660, 665 are located nearby but does not serve to indicate that a switch in direction of coding occurs. Thus coding continues beyond the trigger symbol 680 in the same direction. In the embodiment of FIG. 7e, this is a forward coding direction however continuous reverse coding is also possible.

Figure 7F:
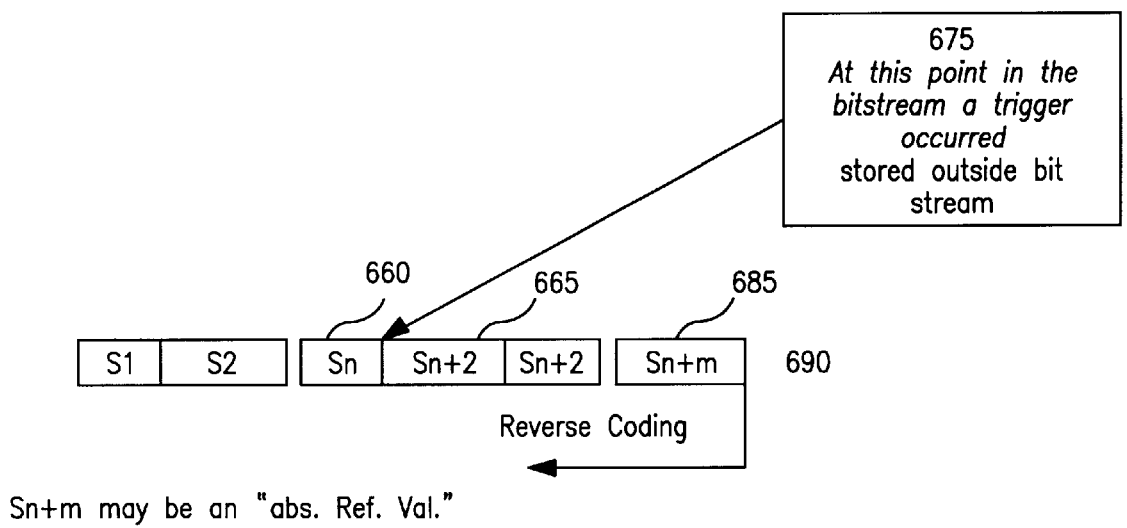

In FIG. 7f, trigger symbol 675 is a unique pointer external to bit stream 690. Trigger symbol 675 may be, for example, a unique bit pattern. Trigger symbol 675 points out that "at this point in bit stream 690, a trigger occurred". In the embodiment shown in FIG. 7f, reverse coding is occurring beginning at absolute reference value 685. Trigger symbol 675 external to bit stream 690 may serve to indicate that absolute signal values 660, 665 are located nearby to the point indicated by trigger symbol 675. However trigger symbol 675 does not serve to indicate that a switch in direction of coding occurs. Thus coding continues beyond the point indicated by trigger symbol 675 in the same direction. In the embodiment of FIG. 7f, this is a reverse coding direction however continuous forward coding is also possible.

Figure 8:
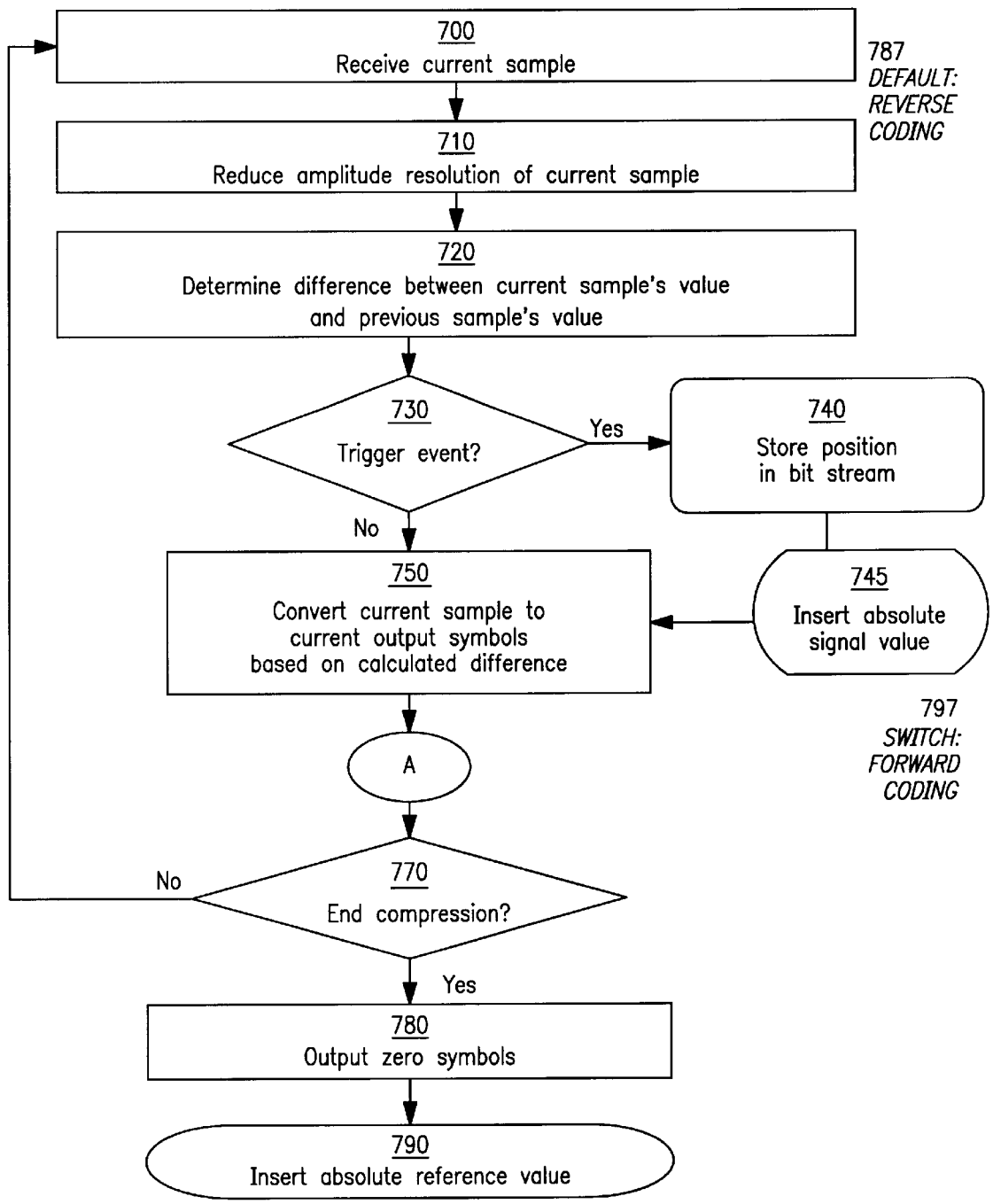
FIG. 8 is a flow diagram of one embodiment of a method for compressing data in accordance with the present invention.

FIG. 8 is a flow diagram of one embodiment of a method for compressing data in accordance with the present invention. As discussed above, the method of the present invention may be performed under the control of any appropriate computer algorithm stored in a memory or a portion of a memory of microprocessor 51, 64 and/or microcomputer circuit 58 in IMD 10. Such a computer algorithm may be any program capable of being stored in an electronic medium such as, by way of example only, RAM 68 or ROM 70 of IMD 10, where the contents of RAM 68 and ROM 70 may be accessed and consequently executed by microprocessor 51, 64 and/or microcomputer circuit 58.

At block 700, a current sample is received. This sample may be for example, one or more data streams as described above or one or more components of such a data stream. The current sample may be, for example, a digital sample. The current sample may be, for example, a digital value representing the amplitude of a certain analog signal that is obtained from the heart, including, but not limited to an Intra cardiac electrogram. In one embodiment of the invention, the current sample is an IEGM snapshot as described above. In another embodiment of the invention, the IEGM snapshot consists of a plurality of digitized samples, which may be processed one at a time; in this embodiment, the current sample is one of the plurality of digitized samples. The sample may be received, for example, by microprocessor 51, 64 or microcomputer circuit 58 of IMD 10.

At block 710, the amplitude resolution of the current sample is reduced. In one embodiment of the invention, this is accomplished by dividing the digital sample by $2^n$ where n is equal to (0), 1, 2 . . . .

At block 720, the difference between the value of the current sample and the value of the previous sample is determined.

In one embodiment of the invention, this is determined using $$d[n]=x[n-1]-x[n]$$

where d[n] equals the difference signal, x[n] is the value of the current sample and x[n−1] is the value of the previous sample. This embodiment may be used, for example, for reverse coding as described above and indicated at 797 in FIG. 8.

In another embodiment of the invention, this is determined using $$d[n]=x[n]-x[n-1]$$

where d[n] equals the difference signal, x[n] is the value of the current sample and x[n−1] is the value of the previous sample. This embodiment may be used, for example, for forward coding as described above and indicated at 787 in FIG. 8.

In one embodiment of the invention, the difference signal has less variance than the value of the current sample. The difference signal may thus be more efficiently encoded using entropy encoding than the value of the current sample.

At block 730, it may be determined if a trigger event should be represented in the data stream being encoded. If a trigger event has not occurred, compression may continue in the same manner. If a trigger event has occurred, at block 740 the current position in the bit stream may be stored. In one embodiment of the invention, this position is stored by inserting a uniquely identifiable bit pattern into the bit stream. Subsequently an absolute signal value may be encoded into the bit stream as seen at block 745.

This absolute signal value may be a reference value indicating a significant event in the encoded data stream, including, but not limited to the point at which a trigger event occurred in the stream, the point of a "markedly different" value and the point at which reversal of encoding took place. For example, absolute signal value 645 may correspond to a point at which encoding has changed from reverse to forward coding as indicated, for example at 797. In at least some embodiments of the invention as described above, absolute signal value encodes an actual signal and may be used to reconstruct data stream 603. Alternatively, absolute signal value may also serve to indicate the beginning or end of bit stream 690.

At block 750, the current sample may be converted to a limited set of output symbols. In one embodiment of the invention, as indicated at A, the difference between the current and previous sample acts as a first stage determination on how the current sample is to be converted to a limited set of output symbols. These symbols may be abstract representations of numerical values. These symbols may comprise more than one character or may be a single character. For example, in one embodiment of the invention, the symbols may be:

$$Symbol_{set} = \{-2\_symbol, -1\_symbol, 0\_symbol, 1\_symbol, 2\_symbol\}$$

Thus a numerical 0 may be represented by 0_symbol.

Meanwhile a numerical 9 may be represented by $2\_symbol, 2\_symbol, 2\_symbol, 2\_symbol, 1\_symbol$.

In another embodiment of the invention, an escape symbol is coded followed by the actual numerical value of the signal. As described previously, the symbol set described above is only one possible set for use in accordance with the present invention. The choice of the symbol set and the choice of which symbols map to which bit pattern may dictate a different set of rules which are still contemplated by the present invention. A different symbol set will comprise different corresponding bit patterns and will also provide different criteria for whether a difference value is "markedly different."

The limited set of output symbols allows the use of a small set of variable bit length codes. Small numerical values may be converted into a single symbol. Meanwhile, large numerical values may be converted into a stream of symbols.

The current sample may be converted to output symbols in any suitable manner. One embodiment of a subroutine for this conversion, as indicated at A, is described further with reference to FIG. 9.

However the current sample is converted, at block 770 it is determined whether compression should end. If compression continues, the method may proceed to block 700 and receive a new current sample. If compression ends, the method may proceed to block 780 where the number of zero symbols still present within the system are outputted. Some embodiments of a mechanism for outputting the zero symbols are described further below with reference to FIG. 9.

At block 790, an absolute reference value may be inserted. In one embodiment of the invention, this absolute reference value is inserted at the end of the sample stream. In some embodiments of the invention, he absolute reference value may be used to reconstruct the actual sample values. This absolute reference value may be used as described in FIG. 6, for example to indicate a significant event in the encoded data stream, including, but not limited to the point at which a trigger event occurred in the stream, the point at which reversal of encoding took place, the start-of-encoding position, and/or the end-of-encoding position.

Figure 9:
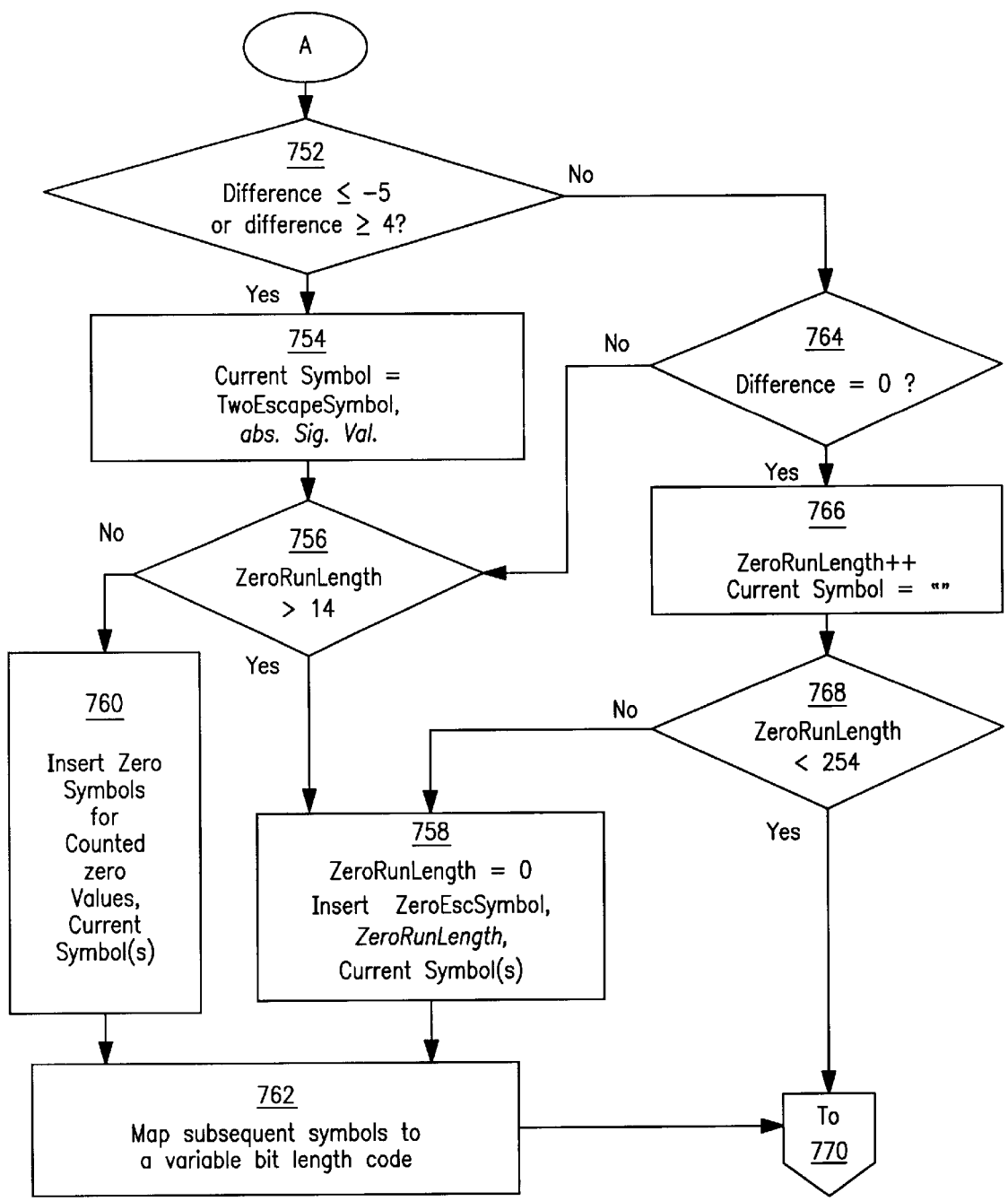
FIG. 9 is a flow diagram of one embodiment of a subroutine of a method for compressing data in accordance with the present invention.

FIG. 9 shows a flow diagram of one embodiment of a subroutine of a method for compressing data in accordance with the present invention at A.

At block 752, it may be determined if the difference value lies between two predetermined values. This difference value may be, for example, the value determined at block 720 above. For example, it may be determined if the difference value is less than or equal to a first predetermined value and/or greater than or equal to a second predetermined value. In the embodiment of FIG. 8, the predetermined values are −5 and 4, respectively. If the difference value does not lie between the two predetermined values, the subroutine may proceed to 764. If the difference value lies between the two predetermined values, the routine may proceed to block 754.

At block 754, a current symbol may be calculated for the difference value. In the embodiment of FIG. 8, the current symbol is calculated based on the formula Current symbol=twoescapesymbol, absolute signal value
where "twoescapesymbol" is an abstract unique symbol that may be converted to a bit pattern at 762 and "absolute signal value" is the bit pattern denoting the reduced amplitude sample value (for example, from stream 603).

The routine may then proceed to block 756, where it may be determined if long runs of sequential zero values are present. In one embodiment of the invention, a long run is a set of sequential zero values comprising more than 14 zero values. Blocks 764, 766, 768 and 758 support the determination of the occurrence of such a run. These will be discussed further below.

If a long run of zero values is found, the routine may proceed to block 758 where a zero escape symbol followed by a bit pattern denoting the actual number of encountered zero values are inserted followed by the current symbol or symbols. If a smaller run of zero values is found, the routine may proceed to block 760 where for each zero value a zero symbol is inserted followed by the current symbol or symbols.

The routine may then proceed to block 762, where the symbols generated at block 760 are mapped to a variable bit length output code. Statistical analysis may be used to determine the probability of the occurrence of any given output symbol. The code may then be based on this analysis. For example, the encoding of symbols may be chosen in such a way that the symbol with the highest probability of occurrence is assigned the shortest code sequence.

In one embodiment of the invention, the following symbol set, including escape codes is used:

| | |
|---|---|
| −2_symbol | 4 bit sequence |
| −1_symbol | 2 bit sequence |
| 0_symbol | 1 bit sequence |
| 1_symbol | 3 bit sequence |
| 2_symbol | 5 bit sequence |
| 0_RLL_escape symbol | 6 bit sequence |
| 2_RLL_escape symbol | 6 bit sequence |

As stated above, blocks 764, 766, 768 and 758 support the determination of the occurrence of a run of sequential zero symbols.

At block 764, it may be determined if the difference value evaluated at 752 equals zero. If the difference value equals zero, the routine proceeds to block 766, where the number of zero's that have been processed so far is tracked. At block 766, the current symbol may also be reset to empty.

If the difference value does not equal zero, the routine may proceed to block 756 and from there may proceed as described above.

At block 768, it may be determined if the zero run length exceeds a predetermined value. In one embodiment of the invention, the predetermined value is 254. In other words, the zero run length is limited, for example, the run of zero symbols is limited to 255. In the embodiment shown in FIG. 8, the current implementation generates an 8-bit output so the run length of zero symbols is limited to $2^8-1$ or 254. If the zero run length does not exceeds the predetermined value, the subroutine returns to block 770 as described above.

Alternatively, as shown at block 758, if the zero run length does exceed the predetermined value, an escape symbol may be generated and immediately followed by a 8-bit pattern that indicates the number of counted zero values. Followed by the already determined current symbol or symbols.

From block 758, the routine may then proceed to block 762 as described above where the generated symbols may be mapped to a variable bit length output code. At this point, a mixed stream of information results, consisting on the one hand of abstract "symbols" and on the other hand of numerical values represented by bit patterns. Block 762 converts the remaining symbols in the mixed stream to bit patterns. Once block 762 is completed, a bit stream results rather than a mixed stream of symbols and bits.

The bit patterns generated in this manner may be uniquely identified in the resulting bit stream. In one embodiment of the invention, identification of the bit patterns representing the symbols can only be accomplished from one direction. In order to decode the compressed bit stream starting from the last bit pattern that was generated towards the first bit pattern that was generated, the value of bit[m−1] depends on bit[m]. This is the case, for example, in the reversed coding process. Alternatively, the value of bit[m+1] depends on bit[m] This may be the case, in order to decode the compressed bit stream starting at the first bit pattern that was generated toward the last bit pattern that was generated, i.e., in the forward coding process.

In the embodiment of the invention seen in FIGS. 6 through 9, the values determined include: current sample values, previous sample values, difference between current sample and previous sample values, occurrence of trigger events, occurrence of reversal in encoding, start-of-encoding occurrence, end-of-encoding occurrence, presence of long runs of similar symbols in a data stream, absolute signal values and absolute reference values. One or any suitable combination of these values may be varied in accordance with the present invention. Moreover, although the values are shown as being determined in a given order, these values may be determined in any combination and in any order in accordance with the present invention.

The preceding specific embodiments are illustrative of the practice of the invention. It is to be understood, therefore, that other expedients known to those skilled in the art or disclosed herein, may be employed without departing from the invention or the scope of the appended claims. For example, the present invention is not limited to a method for increasing a pacing parameter of a mammalian heart. The present invention is also not limited to the compression and storage of pacing data, per se, but may find further application as a data compression and/or storage means. The present invention further includes within its scope methods of making and using the data compression and/or storage means described hereinabove.

In the claims, means-plus-function clauses are intended to cover the structures described herein as performing the recited function and not only structural equivalents, but also equivalent structures. Thus, although a nail and a screw may not be structural equivalents in that a nail employs a cylindrical surface to secure wooden parts together, whereas a screw employs a helical surface, in the environment of fastening wooden parts a nail and a screw are equivalent structures.

We claim:

1. A method for compressing data in an implantable device, comprising the steps of:
    receiving a current data sample; determining a difference value between the current data sample and a previous data sample;
    converting a sequence of similar output symbols to an escape output symbol; and
    compressing the current data sample to at least one output symbol based on the difference value between the current sample and the previous data sample.

2. The method of claim 1 wherein the output symbol is a compressed bit pattern.

3. The method of claim 1 wherein the output symbol comprises more than one character.

4. The method of claim 1 further comprising:
    reducing the amplitude resolution of the current data sample.

5. The method of claim 1 further comprising:
    converting the output symbol to a variable bit length code.

6. The method of claim 1 wherein the output symbol is a 0 symbol, further comprising:
    converting the output symbol to a 1 bit sequence.

7. The method of claim 1 wherein the output symbol is a 1_symbol, further comprising:
    converting the output symbol to a 3 bit sequence.

8. The method of claim 1 wherein the output symbol is a 0_RLL-escape_symbol, further comprising:
    converting the output symbol to a 6 bit sequence.

9. The method of claim 1 wherein the output symbol 2_RLL-escape_symbol, further comprising:
    converting the output symbol to a 6 bit sequence.

10. The method of claim 1 further comprising:
    inserting an absolute signal value after the current sample.

11. The method of claim 1 further comprising:
    determining if a trigger event has occurred.

12. The method of claim 11 further comprising:
    inserting a trigger symbol as the output symbol to indicate a point at which the trigger event occurred.

13. The method of claim 1 wherein the difference value is zero.

14. The method of claim 13, further comprising:
    compressing the current data sample such that the output symbol is bit pattern 0.

15. The method of claim 1, further comprising:
    compressing the current data sample such that the output symbol is bit pattern 0.

16. The method of claim 1 wherein the difference value indicates that the current data sample has a value of one less than the previous data sample.

17. The method of claim 1 wherein the difference value indicates that the current data sample has a value of one more than the previous data sample.

18. The method of claim 1 wherein the difference value indicates that the current data sample has a value of two less than the previous data sample.

19. The method of claim 1 wherein the difference value indicates that the current date sample has a value of two more than the previous data sample.

20. The method of claim 1 wherein the difference value indicates that the current data sample has a value of three less than the previous data sample.

21. The method of claim 1 wherein the difference value indicates that the current data sample has a value of three more than the previous data sample.

22. The method of claim 21, further comprising:
compressing the current data sample such that the output symbol is bit pattern 11110 followed by bit pattern 110.

23. The method of claim 1, further comprising:
compressing the current data sample such that the output symbol is bit pattern 11110 followed by bit pattern 110.

24. The method of claim 1 wherein the difference value indicates that the current data sample has a value of four less than the previous data sample.

25. The method of claim 24, further comprising:
compressing the current data sample such that the output symbol is bit pattern 1110 110 followed by bit pattern 110.

26. The method of claim 1, further comprising:
compressing the current data sample such that the output symbol is bit pattern 1110 110 followed by bit pattern 110.

27. The method of claim 1, wherein the difference values comprises a plurality of sequential zeroes.

28. The method of claim 27, further comprising:
compressing the current data sample such that the output symbol is 111110 followed by a binary value of the plurality of sequential zeroes.

29. The method of claim 1, further comprising:
compressing the current data sample such that the output symbol is 111110 followed by a binary value of the plurality of sequential zeroes.

30. The method of claim 1, wherein the difference value indicates that the current data sample has a markedly different value than the previous data sample.

31. The method of claim 30, comprising:
compressing the current data sample such that the output symbol is bit pattern 111111 followed by a binary value of the current data sample.

32. The method of claim 30, further comprising:
compressing the current data sample such that the output symbol is bit pattern 111111 followed by a binary value of the difference value.

33. The method of claim 1, further comprising:
compressing the current data sample such that the output symbol is bit pattern 111111 followed by a binary value of the current data sample.

34. The method of claim 1, further comprising:
compressing the current data sample such that the output symbol is bit pattern 111111 followed by a binary value of the difference value.

35. The method of claim 1 wherein the difference value has a value of greater than four.

36. The method of claim 1 wherein the difference value has a value of less than negative five.

37. An implantable medical device comprising:
a processor;
at least one sensor operably connected to the processor for collecting at least one data sample;
wherein
the processor receives a current data sample, determines a difference value between the current data sample and a previous data samples, converts a sequence of similar output symbols to an escape output symbol and compresses the current data sample to at least one output symbol based on the difference value.

38. The device of claim 37, further comprising:
a memory location operably connected to the processor for storing the data sample.

39. The device of claim 37, further comprising:
a memory location operably connected to the processor for storing the difference value.

40. The device of claim 37, further comprising:
a converter operably connected to the processor for converting at least one signal to the data sample.

41. An implantable medical system, comprising:
means for receiving a current data sample;
means for determining a difference value between the current data sample and a previous data sample;
means for converting a sequence of similar output symbols to an escape output symbol; and
means for compressing the current data sample to at feast one output symbol based on the difference value between the current sample and the previous data sample.

42. The system of claim 41 wherein the output symbol is a compressed bit pattern.

43. The system of claim 41 wherein the output symbol comprises more than one character.

44. The system of claim 41 further comprising:
means for reducing the amplitude resolution of the current data sample.

45. The system of claim 41 wherein the output symbol is a 0_RLL-escape_symbol, further comprising:
means for converting the output symbol to a 6 bit sequence.

46. The system of claim 41 wherein the output symbol is a 2_RLL-escape_symbol, further comprising:
means for converting the output symbol to a 6 bit sequence.

47. The system of claim 41 further comprising:
means for inserting an absolute signal value after the current sample.

48. The system of claim 41 further comprising:
means for determining if a trigger event has occurred.

49. The system of claim 48 further comprising:
means for inserting a trigger symbol as the output symbol to indicate a point at which the trigger event occurred.

50. The system of the claim 41 wherein the difference value is zero, further comprising:
means for compressing the current data sample such that the output symbol is bit pattern 0.

51. The system of claim 41, further comprising:
means for compressing the current data sample such that the output symbol is bit pattern 0.

52. A computer usable medium including a program for compressing data in an implantable device, comprising:
computer program code that receives a current data sample;
computer program code that determines a difference value between the current data sample and a previous data sample;
computer program code that converts a sequence of similar output symbols to en escape output symbol; and
computer program code that compresses the current data sample to at least one output symbol based on the difference value between the current sample and the previous data sample.

53. The program of claim 52 wherein the output symbol is a compressed bit pattern.

54. The program of claim 52 wherein the output symbol comprises more than one character.

55. The program of claim 52 further comprising:

computer program code that reduces the amplitude resolution of the current data sample.

56. The program of claim 52 further comprising:

computer program code that converts the output symbol to a variable bit length code.

57. The program of claim 52 wherein the output symbol is a −2_symbol, further comprising:

computer program code that converts the output symbol to a 4 bit sequence.

58. The program of claim 52 wherein the output symbol is a 0 symbol, further comprising:

computer program code that converts the output symbol to a 1 bit sequence.

59. The program of claim 52 wherein the output symbol is a 1_symbol, further comprising:

computer program code that converts the output symbol to a 3 bit sequence.

60. The program of claim 52 further comprising:

computer program code that inserts an absolute signal value after the current sample.

61. The program of claim 52 further comprising:

computer program code that determines it a trigger event has occurred.

62. The program of claim 61 further comprising:

computer program code that inserts a trigger symbol as the output symbol to indicate a point at which the trigger event occurred.

63. The program of claim 52 wherein the difference value is zero, further comprising:

computer program code that compresses the current data sample such that the output symbol is bit pattern 0.

64. The program of claim 52, further comprising:

computer program code that compresses the current data sample such that the output symbol is bit pattern 0.

* * * * *

UNITED STATES PATENT AND TRADEMARK OFFICE
CERTIFICATE OF CORRECTION

PATENT NO.    : 6,719,689 B2  
DATED         : April 13, 2004  
INVENTOR(S)   : Munneke and Kerver It is certified that error appears in the above-identified patent and that said Letters Patent is hereby corrected as shown below:

Column 27,
Line 64, delete "data samples", replace with -- data sample --.

Column 30,
Line 6, delete "it a trigger", replace with -- if a trigger --.

Signed and Sealed this

Eighteenth Day of January, 2005

JON W. DUDAS  
*Director of the United States Patent and Trademark Office*